United States Patent [19]
Meyer et al.

[11] Patent Number: 5,859,190
[45] Date of Patent: Jan. 12, 1999

[54] COMBINATORIAL LIBRARIES OF HYDANTOIN AND THIOHYDANTOIN DERIVATIVES, METHODS OF MAKING THE LIBRARIES AND COMPOUNDS THEREIN

[75] Inventors: Jean-Philippe Meyer, Holland, Pa.; John M. Ostresh, Encinitas; Richard A. Houghten, Del Mar, both of Calif.

[73] Assignee: Trega Biosciences, Inc., San Diego, Calif.

[21] Appl. No.: 794,363

[22] Filed: Feb. 4, 1997

[51] Int. Cl.$^6$ .................................. C07K 1/04; C07K 4/00
[52] U.S. Cl. ....................... 530/331; 530/333; 530/334; 530/335; 525/54.1; 525/54.11; 548/317.1; 548/319.5
[58] Field of Search ................... 525/54.1, 54.11; 530/333, 334, 335, 331; 548/317.1, 319.5

[56] References Cited

U.S. PATENT DOCUMENTS

| | | | |
|---|---|---|---|
| 5,389,614 | 2/1995 | Konis et al. | 514/18 |
| 5,612,002 | 3/1997 | Cody et al. | 422/131 |

OTHER PUBLICATIONS

Butain et al., J. Chem. Soc. Trans. I (1988) pp. 3175–3182.
Esser et al., Angew. Chem. vol. 90, No. 6 (1978) pp. 495–496.
DeWitt et al., "'Diversomers'": An approach to nonpeptide, nonoligomeric chemical diversity. *Proc. Natl. Acad. Sci.*, 90:6909–6913 (1993).
DeWitt and Czarnik, "Combinatorial Organic Synthesis Using Parke–Davis's Diversomer Method." *Acc. Chem. Res.*, 29(3) :114–122 (1996).
Hanessian and Yang, "Solution and Solid Phase Synthesis of 5–Alkoxyhydantoin Libraries with a Three–Fold Functional Diversity." *Tetrahedron Letters*, 37(33) :5835–5838 (1996).
Dressman et al., "Solid Phase Synthesis of Hydantoins Using a Carbamate Linker and a Novel Cyclization/Cleavage Step." *Tetrahedron Letters*, 37(7) :937–940 (1996).
Ostresh et al., "Peptide Libraries: Determination of Relative Reaction Rates of Protected Amino Acids in Competitive Couplings." *Biopolymers.*, 84:1661–1689 (1994).
Gordon et al., "Applications of combinatorial technologies to drug discovery. 2. Combinatorial organic synthesis, library screening strategies, and future directions." *J. of Med. Chem.*, 37(10) :1386–1401 (1994).
Gallop et al., "Applications of combinatorial technologies to drug discovery. 1. Background and peptide combinatorial libraries." *J. of Med.Chem.*, 37(9) :1233–1251 (1994).
Ostresh et al., "Libraries from libraries: Chemical transformation of combinatorial libraries to extend the range and repertoire of chemical diversity." *Proc. Natl., Acad. Sci. USA*, 9:11138–11142 (1994).
Pinilla et al., "Rapid Identification of High Affinity Peptide Ligands Using Positional Scanning Synthetic Peptide Combinatorial Libraries." *BioTecniques*, 13(6) :901–905 (1992).
Houghten et al., "Generation and use of synthetic peptide combinatorial libraries for basic research and drug discovery." *Nature*, 354:84–86 (1991).

*Primary Examiner*—Cecilia J. Tsang
*Assistant Examiner*—Bennett Celsa
*Attorney, Agent, or Firm*—Campbell & Flores LLP

[57] ABSTRACT

The invention provides a rapid approach for combinatorial synthesis and screening of libraries of hydantoin and thiohydantoin compounds. The present invention further provides the compounds made by the combinatorial synthesis.

25 Claims, 6 Drawing Sheets

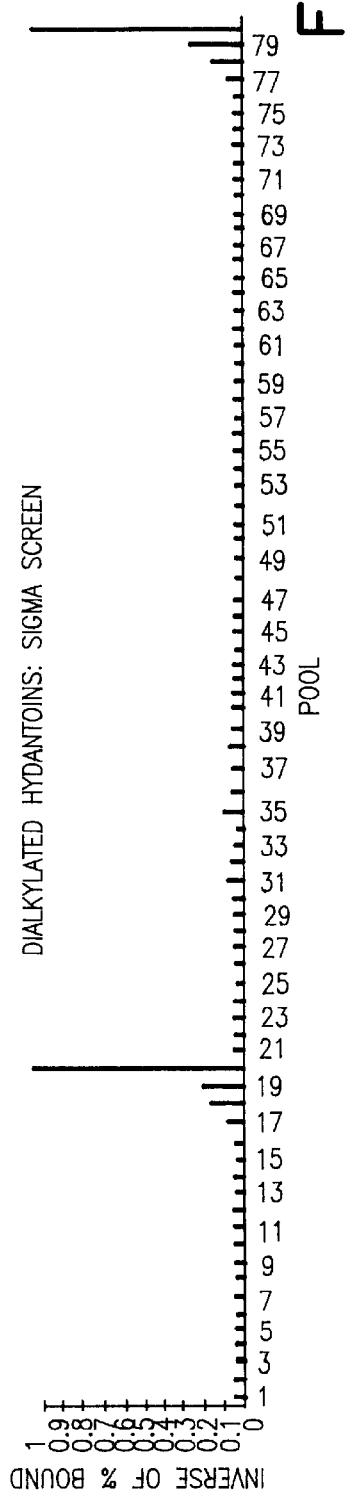
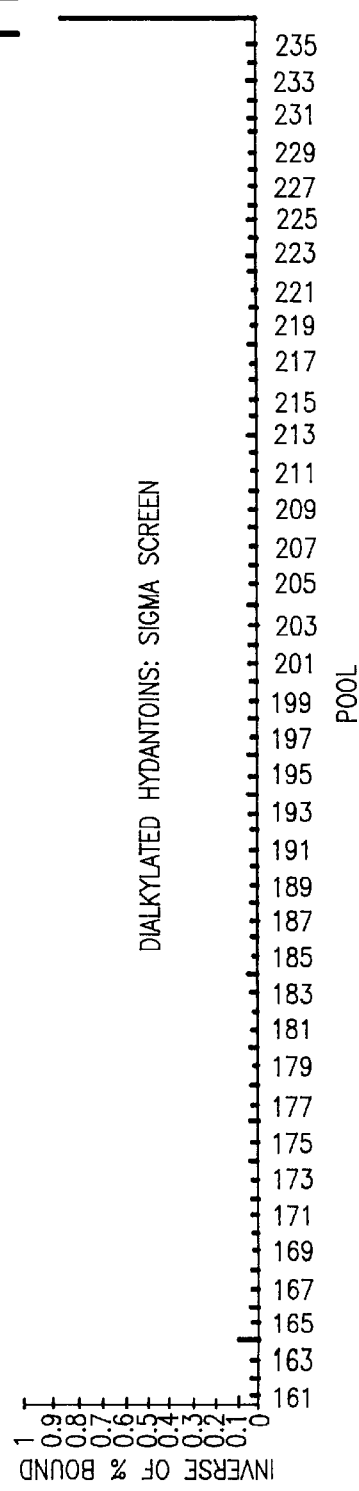
FIG. 3A
FIG. 3B
FIG. 3C

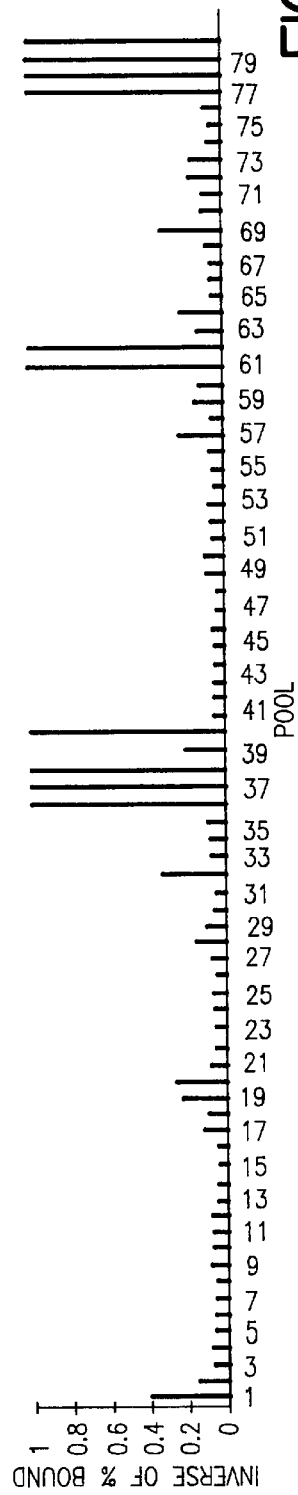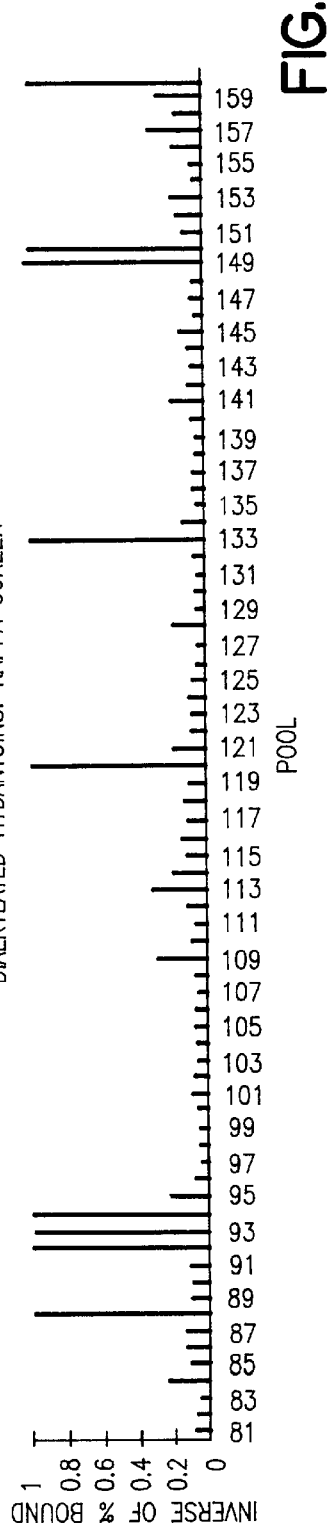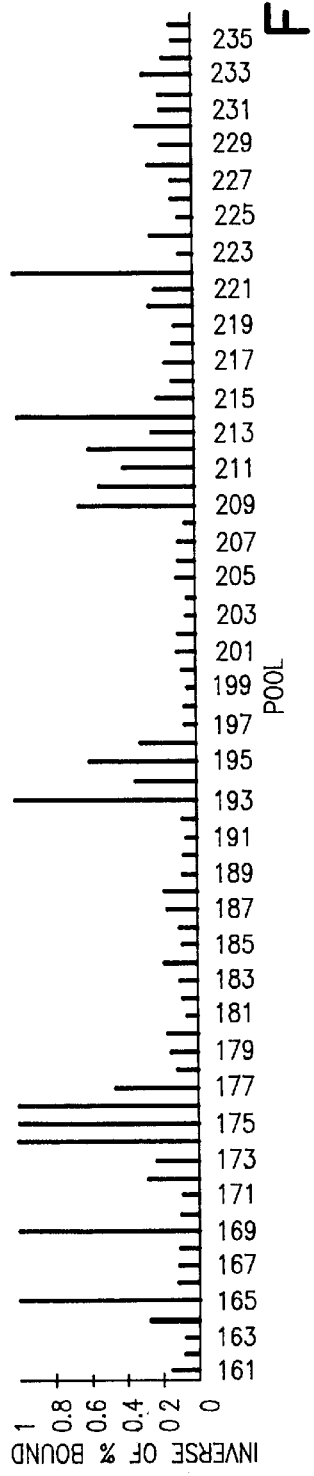

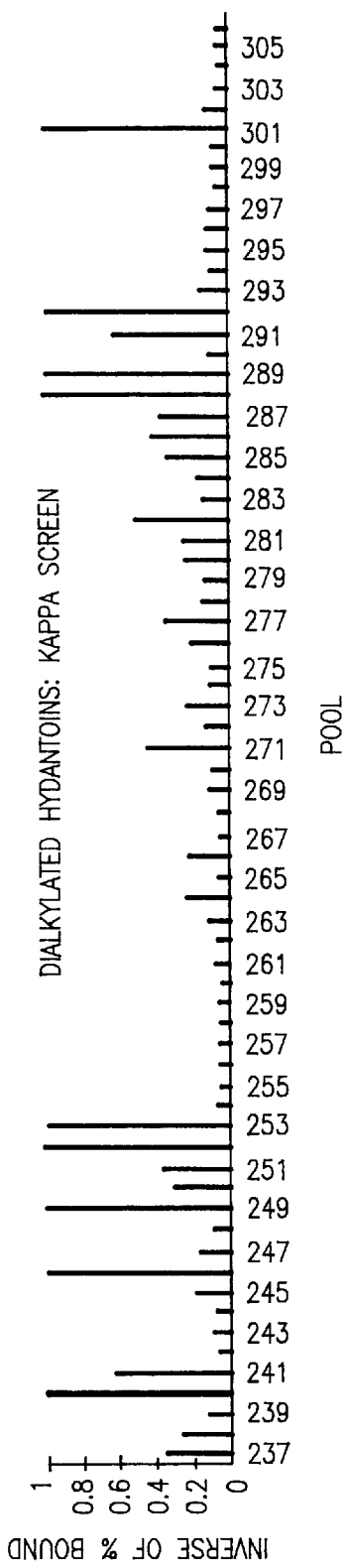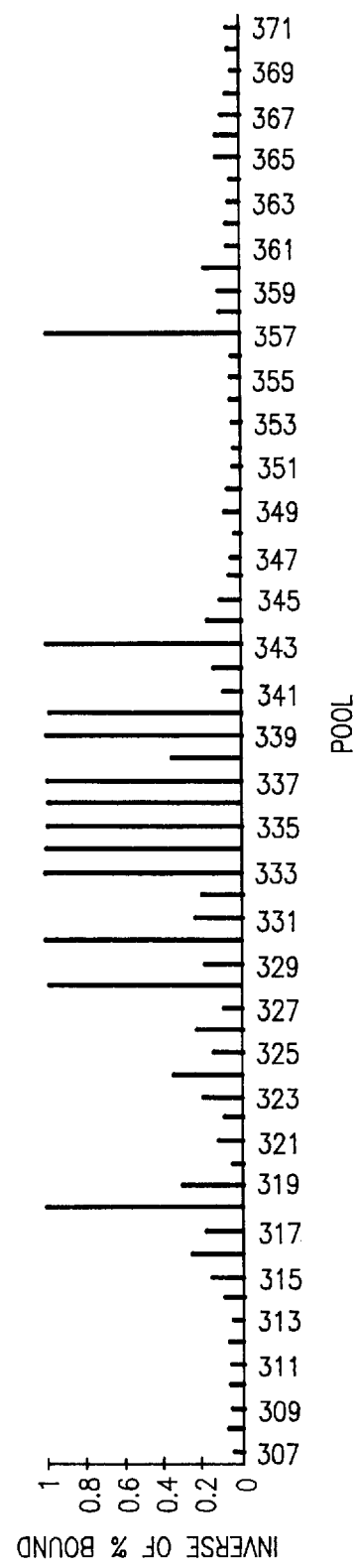

COMBINATORIAL LIBRARIES OF HYDANTOIN AND THIOHYDANTOIN DERIVATIVES, METHODS OF MAKING THE LIBRARIES AND COMPOUNDS THEREIN

BACKGROUND OF THE INVENTION

FIELD OF THE INVENTION

The present invention relates generally to the combinatorial synthesis of hydantoin derivatives. More specifically, the invention provides novel hydantoins and thiohydantoins as well as novel combinatorial libraries comprised of many such compounds, and methods of synthesizing the libraries.

BACKGROUND INFORMATION

The process of discovering new therapeutically active compounds for a given indication involves the screening of all compounds from available compound collections. From the compounds tested one or more structure(s) is selected as a promising lead. A large number of related analogs are then synthesized in order to develop a structure-activity relationship and select one or more optimal compounds. With traditional one-at-a-time synthesis and biological testing of analogs, this optimization process is long and labor intensive. Adding significant numbers of new structures to the compound collections used in the initial screening step of the discovery and optimization process cannot be accomplished with traditional one-at-a-time synthesis methods, except over a time frame of months or even years. Faster methods are needed that allow for the preparation of up to thousands of related compounds in a matter of days or a few weeks. This need is particularly evident when it comes to synthesizing more complex compounds, such as the hydantoin and thiohydantoin compounds of the present invention.

Solid-phase techniques for the synthesis of peptides have been extensively developed and combinatorial libraries of peptides have been generated with great success. During the past four years there has been substantial development of chemically synthesized combinatorial libraries (SCLs) made up of peptides. The preparation and use of synthetic peptide combinatorial libraries has been described, for example, by Dooley in U.S. Pat. No. 5,367,053, Huebner in U.S. Pat. No. 5,182,366, Appel et al. in WO PCT 92/09300, Geysen in published European Patent Application 0 138 855 and Pirrung in U.S. Pat. No. 5,143,854. Such SCLs provide the efficient synthesis of an extraordinary number of various peptides in such libraries and the rapid screening of the library which identifies lead pharmaceutical peptides.

Peptides have been, and remain, attractive targets for drug discovery. Their high affinities and specificities toward biological receptors as well as the ease with which large peptide libraries can be combinatorially synthesized make them attractive drug targets. The screening of peptide libraries has led to the identification of many biologically-active lead compounds. However, the therapeutic application of peptides is limited by their poor stability and bioavailability in vivo. Therefore, there is a need to synthesize and screen compounds which can maintain high affinity and specificity toward biological receptors but which have improved pharmacological properties relative to peptides.

Combinatorial approaches have recently been extended to "organic," or non-peptide, libraries. The organic libraries to the present, however, are of limited diversity and generally relate to peptidomimetic compounds; in other words, organic molecules that retain peptide chain pharmacophore groups similar to those present in the corresponding peptide.

Although the present invention is principally derived from the synthesis of dipeptides, the dipeptides are substantially modified. In short, they are chemically modified through alkylation and cyclization into the subject hydantoins, thus providing mixtures and individual compounds of substantial diversity.

Significantly, many biologically active compounds contain hydantoins. Hydantoins have been reported by Hanessian and Yang, *Tet. Lett.*, 37:5835 (1996), to be useful as anticonvulsants, antiarrhythmics and antidiabetics as well as having herbicidal and fungicidal activity. Because hydantoin moieties are found in many biologically active compounds and are known to have useful therapeutic implications, there is a need to further study and develop large numbers of hydantoins and their binding to biological receptors.

Relatively small solid-phase hydantoin libraries have been prepared previously, as described for instance in DeWitt et al., *Proc. Natl. Acad. Sci.*, 90:6909 (1993), DeWitt et al., *Acc Chem. Res.*, 29:114 (1996), Dressman et al., *Tet. Lett.*, 37:937 (1996) and Hanessian and Yang, supra. To date, however, the libraries comprise only a single amino acid moiety and, therefore, of limited diversity compared to the present invention. Moreover, linkers previously used to attach amino acids to the solid-phase resin, such as the carbamate linkers used by Dressman and DeWitt, are bulky and can hinder the hydantoin cyclization, further limiting the ability to diversify as needed in the study of hydantoins.

This invention satisfies these needs and provides related advantages as well. The present invention overcomes the known limitations to classical organic synthesis of hydantoins as well as the shortcomings of combinatorial chemistry with small organics or peptidomimetics. Moreover, the present invention provides a large array of diverse hydantoins which can be screened for biological activity, and as described below, are biologically active.

SUMMARY OF THE INVENTION

The invention provides a rapid approach for combinatorial synthesis and screening of libraries of hydantoin and thiohydantoin compounds. The present invention further provides the compounds made by the combinatorial synthesis. More specifically, the present invention relates to the generation of synthetic combinatorial libraries of organic compounds based on the formula:

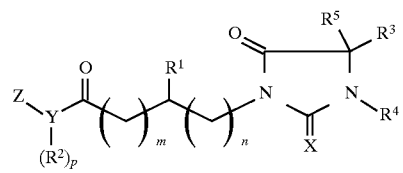

wherein $R^1$, $R^2$, $R^3$, $R^4$, $R^5$, X, Y, Z, m, n and p have the meanings provided below.

BRIEF DESCRIPTION OF THE DRAWINGS

FIG. 4 provides graphs depicting the K-opioid receptor screening data for the di-alkylated hydantoin library as exemplified in Example VI.

DETAILED DESCRIPTION OF THE INVENTION

Figure 1:
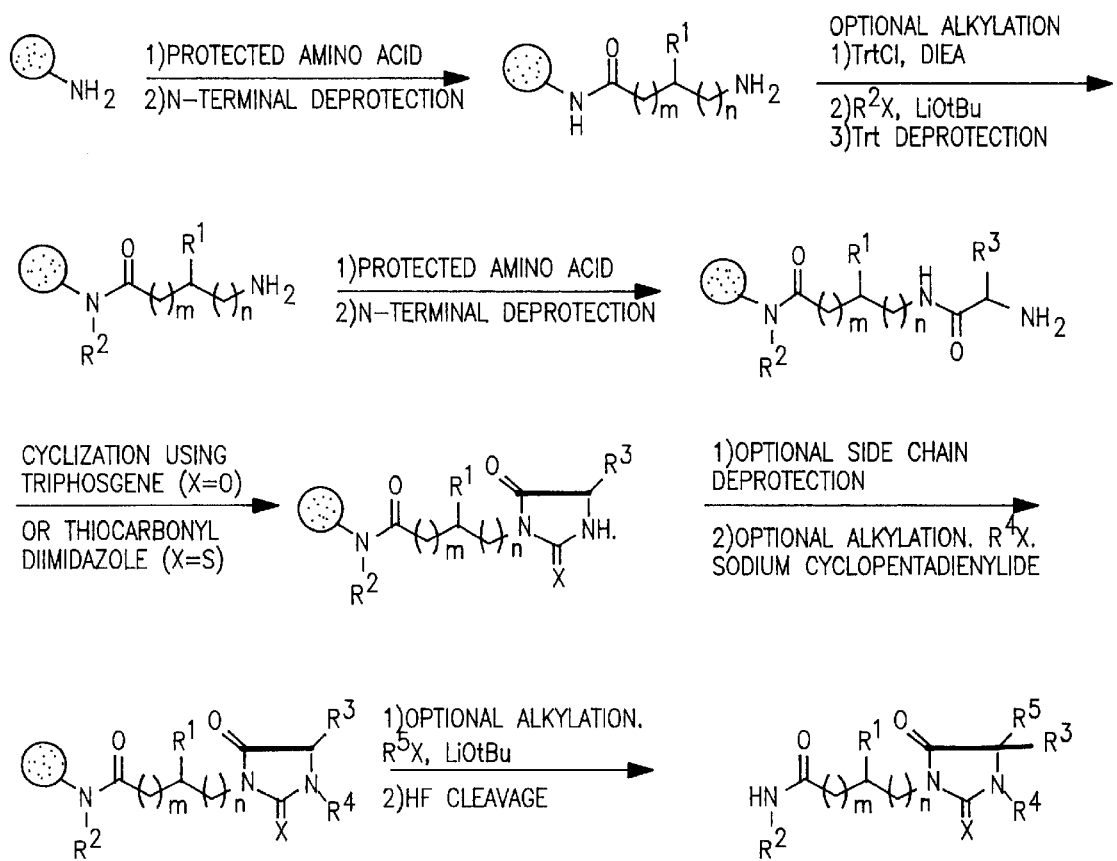
FIG. 1 shows the Reaction Scheme I for preparing libraries and compounds of the present invention.

The present invention relates to the generation of synthetic combinatorial libraries and individual compounds which are based on the Formula I:

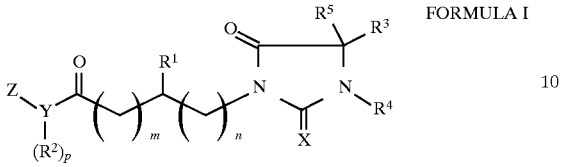

In the above Formula I:

$R^1$ is a hydrogen atom, $C_1$ to $C_{10}$ alkyl; $C_1$ to $C_{10}$ substituted alkyl, $C_7$ to $C_{16}$ phenylalkyl, $C_7$ to $C_{16}$ substituted phenylalkyl, phenyl, substituted phenyl, amino, (monosubstituted) amino, (disubstituted) amino, (trisubstituted)amino, carboxy, substituted carboxy, carbamoyl, substituted carbamoyl, $C_3$ to $C_7$ cycloalkyl, or $C_3$ to $C_7$ substituted cycloalkyl;

$R^2$ is a hydrogen atom, $C_1$ to $C_{10}$ alkyl, $C_2$ to $C_{10}$ alkenyl, benzyl, substituted benzyl, naphthylmethyl, or substituted naphthylmethyl and, preferably, is hydrogen, methyl, ethyl, benzyl, allyl, or naphthylmethyl, more preferably 2-naphthylmethyl, and $R^2$ is most preferably hydrogen, methyl, ethyl, allyl, or benzyl;

$R^3$ is a hydrogen atom, $C_1$ to $C_{10}$ alkyl; $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, or $C_3$ to $C_7$ substituted cycloalkyl;

$R^4$ is a hydrogen atom, $C_1$ to $C_{10}$ alkyl, $C_2$ to $C_{10}$ alkenyl, benzyl, substituted benzyl, naphthylmethyl, or substituted naphthylmethyl and, preferably, is hydrogen, methyl, ethyl, benzyl, allyl, or naphthylmethyl, more preferably 2-naphthylmethyl, and $R^2$ is most preferably hydrogen, methyl, or benzyl;

$R^5$ is hydrogen, $C_1$ to $C_{10}$ alkyl, $C_2$ to $C_{10}$ alkenyl, benzyl, substituted benzyl, naphthylmethyl, or substituted naphthylmethyl and, preferably, is hydrogen, methyl, ethyl, benzyl, allyl, or naphthylmethyl, more preferably 2-naphthylmethyl;

X is an oxygen atom(O) or a sulfur atom(S);

Y is a nitrogen atom (N) or an oxygen atom (O), provided that when Y is nitrogen, p is one and Z is hydrogen or an amino resin and further provided that when Y is oxygen, p is zero and Z is hydrogen or a hydroxy resin;

m is zero to five; and n is zero to four.

In one embodiment of the above hydantoin and thiohydantoin libraries and compounds, the substituents are as follows:

$R^1$ is methyl, benzyl, a hydrogen atom, 2-butyl, aminobutyl, 2-methylpropyl, methylthioethyl, carbamoylmethyl, carbamoylethyl, guanidinopropyl, hydroxymethyl, 1-hydroxyethyl, 2-propyl, 3-indolylmethyl, 4-hydroxybenzyl, 4-chlorobenzyl, ethyl, dimethyl, propyl, butyl, amino, aminopropyl, phenyl, 2-naphthylmethyl, cyclohexylmethyl, 4-nitrobenzyl, cyclohexyl, 4-iodobenzyl, t-butyl, acetamidobutyl, 4-fluorobenzyl, thiomethyl, carboxymethyl, carboxyethyl, N-(2,4-dinitrophenyl)-4-imidazolylmethyl, 2-thienylmethyl, 3-pyridylmethyl, 4-benzoylbenzyl, 4-(fluorenylmethyloxycarbonylamino)benzyl, fluorenylmethyloxycarbonylmethyl, 4-ethoxybenzyl, fluorenylmethyloxycarbonylamino, fluorenylmethyloxycarbonylaminopropyl, fluorenylmethyloxycarbonylaminobutyl, or fluorenylmethyloxycarbonylethyl;

$R^2$, $R^4$ and $R^5$ are each, independently, a hydrogen atom;

$R^3$ is methyl, benzyl, a hydrogen atom, 2-butyl, aminobutyl, 2-methylpropyl, methylthioethyl, guanidinopropyl, hydroxymethyl, 1-hydroxyethyl, 2-propyl, 3-indolylmethyl, 4-hydroxybenzyl, ethyl, dimethyl, propyl, butyl, aminopropyl, phenyl, 2-naphthylmethyl, cyclohexylmethyl, 4-nitrobenzyl, cyclohexyl, 4-iodobenzyl, 4-chlorobenzyl, t-butyl, acetamidobutyl, 4-fluorobenzyl, thiomethyl, carboxymethyl, carboxyethyl, N-(2,4-dinitrophenyl)-4-imidazolylmethyl, 2-thienylmethyl, 3-pyridylmethyl, 4-benzoylbenzyl, fluorenylmethyloxycarbonylmethyl, 4-ethoxybenzyl, fluorenylmethyloxycarbonylaminopropyl, fluorenylmethyloxycarbonylaminobutyl, fluorenylmethyloxycarbonylethyl, 4-(fluorenylmethyloxycarbonylamino)benzyl, or 4-imidazolylmethyl;

X is an oxygen atom(O) or a sulfur atom(S);

Y is a nitrogen atom;

Z is hydrogen or an amino resin;

m is zero to five;

n is zero to four; and p is one.

In one of the preferred embodiments of the present invention, the R groups are those as immediately defined above, when X is an oxygen atom. In yet another preferred embodiment, the R groups are those as immediately defined above and X is a sulfur atom.

In yet further embodiments of the subject hydantoin and thiohydantoin libraries and compounds, the substituents are as follows:

$R^1$ is methyl, carboxymethyl, carboxyethyl, benzyl, a hydrogen atom, N-(2,4-dinitrophenyl)-4-imidazolylmethyl, 2-butyl, aminobutyl, 2-methylpropyl, methylsulfinylethyl, carbamoylmethyl, carbamoylethyl, guanidinopropyl, hydroxymethyl, 1-hydroxyethyl, 2-propyl, N-formyl-3-indolylmethyl, 4-hydroxybenzyl, ethyl, propyl, butyl, aminopropyl, amino, phenyl, 2-naphthylmethyl, cyclohexylmethyl, fluorenylmethyloxycarbonylaminobutyl, methylsulfonylethyl, 4-nitrobenzyl, 4-chlorobenzyl, 4-fluorobenzyl, acetamidobutyl, 3-pyridylmethyl, 2-thienylmethyl, t-butyl, 4-ethoxybenzyl, 4-fluorenylmethyloxycarbonylaminobenzyl, 3-indolylmethyl, fluorenylmethyloxycarbonylmethyl, 4-benzoylbenzyl, 4-iodobenzyl, cyclohexyl, fluorenylmethyloxycarbonylaminopropyl, fluorenylmethyloxycarbonylethyl, 4-imidazolylmethyl, dimethyl, amino, carboxy, fluorenylmethyloxycarbonylamino, carbamoyl, or fluorenylmethyloxycarbonyl;

$R^2$, $R^4$ and $R^5$ are each, independently, a hydrogen atom;

$R^3$ is methyl, carboxymethyl, carboxyethyl, benzyl, a hydrogen atom, N-(2,4-dinitrophenyl)-4-imidazolylmethyl, 2-butyl, aminobutyl, 2-methylpropyl, methylsulfinylethyl, carbamoylmethyl, carbamoylethyl, guanidinopropyl, hydroxymethyl, 1-hydroxyethyl, 2-propyl, N-formyl- 3-indolylmethyl, 4-hydroxybenzyl, ethyl, propyl, butyl, aminopropyl, phenyl, 2-naphthylmethyl, cyclohexylmethyl, fluorenylmethyloxycarbonylaminobutyl, methylsulfonylethyl, 4-nitrobenzyl, 4-chlorobenzyl, 4-fluorobenzyl, acetamidobutyl, 3-pyridylmethyl, 2-thienylmethyl, t-butyl, 4-ethoxybenzyl, 4-fluorenylmethyloxycarbonylaminobenzyl, 3-indolylmethyl, fluorenylmethyloxycarbonylmethyl, 4-benzoylbenzyl, 4-iodobenzyl, cyclohexyl, fluorenylmethyloxycarbonylaminopropyl, fluorenylmethyloxycarbonylethyl, or 4-imidazolylmethyl;

X is an oxygen atom(O) or a sulfur atom(S);

Y is a nitrogen atom;

Z is hydrogen or an amino resin;

m is zero to five;

n is zero to four; and p is one.

In one of the preferred embodiments of the present invention, the R groups are those as immediately defined above, when X is a sulfur atom. In yet another preferred embodiment, the R groups are those as immediately defined above and X is an oxygen atom.

In yet further embodiments of the subject hydantoin and thiohydantoin libraries and compounds, the substituents are as follows:

$R^1$ is methyl, benzyl, a hydrogen atom, 2-butyl, methylaminobutyl, ethylaminobutyl, allylaminobutyl, benzylaminobutyl, 2-methylpropyl, methylsulfinylethyl, N,N-dimethylcarbamoylmethyl, N,N-diethylcarbamoylmethyl, N,N-diallylcarbamoylmethyl, N,N-dibenzylcarbamoylmethyl, N,N-dimethylcarbamoylethyl, N,N-diethylcarbamoylethyl, N,N-diallylcarbamoylethyl, N,N-dibenzylcarbamoylethyl, trimethylguanidinopropyl, triethylguanidinopropyl, triallylguanidinopropyl, benzylguanidinopropyl, dibenzylguanidinopropyl, hydroxymethyl, 1-hydroxyethyl, 2-propyl, N-methyl-3-indolylmethyl, N-ethyl-3-indolylmethyl, N-allyl-3-indolylmethyl, N-benzyl-3-indolylmethyl, 4-hydroxybenzyl, 4-methoxybenzyl, 4-ethoxybenzyl, 4-alloxybenzyl, ethyl, dimethyl, propyl, butyl, methylamino, ethylamino, allylamino, benzylamino, methylaminopropyl, ethylaminopropyl, allylaminopropyl, benzylaminopropyl, phenyl, 2-naphthylmethyl, cyclohexylmethyl, 4-chlorobenzyl, 4-nitrobenzyl, 4-iodobenzyl, 1-methyl-thien-2-ylmethyl, 1-ethyl-thien-2-ylmethyl, 1-allyl-thien-2-ylmethyl, 1-benzyl-thien-2-ylmethyl, 1-methyl-pyrid-3-ylmethyl, 1-ethyl-pyrid-3-ylmethyl, 1-allyl-pyrid-3-ylmethyl, 1-benzyl-pyrid-3-ylmethyl, or 4-fluorobenzyl;

$R^2$ is methyl, ethyl, allyl, or benzyl;

$R^3$ is methyl, benzyl, a hydrogen atom, 2-butyl, aminobutyl, methylaminobutyl, benzylaminobutyl, 2-methylpropyl, methylsulfinylethyl, carbamoylmethyl, carbamoylethyl, guanidinopropyl, trimethylguanidinopropyl, benzylguanidinopropyl, dibenzylguanidinopropyl, hydroxymethyl, 1-hydroxyethyl, 2-propyl, 3-indolylmethyl, N-methyl-3-indolylmethyl, N-benzyl-3-indolylmethyl, 4-hydroxybenzyl, 4-methoxybenzyl, propyl, butyl, phenyl, 2-naphthylmethyl, carboxyethyl, cyclohexylmethyl, 4-chlorobenzyl, 1-methyl-pyrid-3-ylmethyl, 1-ethyl-pyrid-3-ylmethyl, 1-allyl-pyrid-3-ylmethyl, or 1-benzyl-pyrid-3-ylmethyl;

$R^4$ is a hydrogen atom, methyl, or benzyl;

$R^5$ is a hydrogen atom;

X is an oxygen atom(O) or a sulfur atom(S);

Y is a nitrogen atom;

Z is hydrogen or an amino resin;

m is zero to five; and n is zero to four;

p is one.

In one of the preferred embodiments of the present invention, the R groups are those as immediately defined above, when X is an oxygen atom. In yet another preferred embodiment, the R groups are those as immediately defined above and X is a sulfur atom.

In the above Formula the stereochemistry of the chiral $R^1$ through $R^4$ groups can independently be in the R or S configuration, or a mixture of the two. For instance, as will be described in further detail below, the $R^1$ and $R^3$ groups are the side chains of the α-carbon of various natural and synthetic amino acids, except in the case of β-asp, γ-glu, β-Ala, γ-Aba, δ-Orn, ε-Lys, ε-Aca, 7-Aha, isoAsn, and isoGln. The amino acids can be in the L- or D-configuration, resulting in the same R group, varying only in its stereochemistry.

In the above Formula, the term "$C_1$ to $C_{10}$ alkyl" denotes such radicals as methyl, ethyl, n-propyl, isopropyl, n-butyl, sec-butyl, tert-butyl, amyl, tert-amyl, hexyl, heptyl and the like. A preferred "$C_1$ to $C_{10}$ alkyl" group is methyl. Where $C_1$ to $C_{10}$ alkyl is "dimethyl", as for example with an $R^1$ or $R^3$ substituent, it will be appreciated by those in the art that the hydrogen on the ∝-carbon connected to $R^1$ will be absent. Similarly, when $R^3$ is dimethyl, then it is assumed that is equivalent to where both $R^3$ and $R^5$ are each a methyl group.

The term "$C_2$ to $C_{10}$ alkenyl", denotes such radicals as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, as well as dienes and trienes of straight and branched chains, and the like.

The term "$C_2$ to $C_{10}$ alkynyl" denotes such radicals as ethynyl, propynyl, butynyl, pentynyl, hexynyl, heptynyl, as well as di- and tri-ynes.

The term "$C_1$ to $C_{10}$ substituted alkyl," "$C_2$ to $C_{10}$ substituted alkenyl," and "$C_2$ to $C_{10}$ substituted alkynyl," denotes that the above $C_1$ to $C_{10}$ alkyl groups and $C_2$ to $C_{10}$ alkenyl and alkynyl groups are substituted by one or more, and preferably one or two, halogen, hydroxy, protected hydroxy, $C_3$ to $C_7$ cycloalkyl, $C_3$ to $C_7$ substituted cycloalkyl, naphthyl, substituted naphthyl, adamantyl, abietyl, thiofuranyl, indolyl, substituted indolyl, amino, protected amino, (monosubstituted)amino, protected (monosubstituted)amino, (disubstituted)amino, acetamido, guanidino, (monosubstituted)guanidino, (disubstituted) guanidino, (trisubstituted)guanidino, imidazolyl, substituted imidazolyl, pyrolidinyl, $C_1$ to $C_7$ acyloxy, nitro, heterocycle, substituted heterocycle, $C_1$ to $C_4$ alkyl ester, carboxy, carbamoyl, carbamoyloxy, carboxamido, protected carboxamido, fluorenylmethyloxycarbonyl, fluorenylmethyloxycarbonylamino, cyano, methylsulfonylamino, methylsulfinyl, methylsulfonyl, sulhydryl, $C_1$ to $C_4$ alkylthio, $C_1$ to $C_4$ alkyl sulfonyl or $C_1$ to $C_4$ alkoxy groups. The substituted alkyl groups may be substituted once or more, and preferably once or twice, with the same or with different substituents.

Examples of the above substituted alkyl groups include the cyanomethyl, nitromethyl, chloromethyl, hydroxymethyl, tetrahydropyranyloxymethyl, trityloxymethyl, propionyloxymethyl, aminomethyl, carboxymethyl, allyloxycarbonylmethyl, allylcaroxybonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(isopropyl), 2-carbamoyloxyethyl, chloroethyl, bromoethyl, fluoroethyl, iodoethyl, chloropropyl, bromopropyl, fluoropropyl, iodopropyl and the like.

In the preferred embodiments of the subject invention, $C_1$ to $C_{10}$ alkyl, $C_2$ to $C_{10}$ alkenyl, $C_2$ to $C_{10}$ alkynyl, $C_1$ to $C_{10}$ substituted alkyl, $C_2$ to $C_{10}$ substituted alkenyl, or $C_2$ to $C_{10}$ substituted alkynyl groups are preferably present as the $C_1$ to $C_7$ analogs, respectively, and more preferably, as the $C_1$ to $C_6$ analogs. However, it would be appreciated to those of skill in the art that one or a few carbons could be added to an alkyl, alkenyl, alkynyl, substituted or unsubstituted, without substantially modifying the structure and function of the subject compounds and that, therefore, such additions would not depart from the spirit of the invention.

The term "$C_1$ to $C_4$ alkoxy" as used herein denotes groups such as methoxy, ethoxy, n-propoxy, isopropoxy, n-butoxy, t-butoxy and like groups. A preferred $C_1$ to $C_4$ alkoxy group is methoxy.

The term "$C_1$ to $C_7$ acyloxyl" denotes herein groups such as formyloxy, acetoxy, propanoyloxy, butanoyloxy, pentanoyloxy, hexanoyloxy, heptanoyloxy, and the like.

Similarly, the term "$C_1$ to $C_7$ acyl" encompasses groups such as formyl, acetyl, propionoyl, butyroyl, pentanoyl, hexanoyl, heptanoyl, benzoyl and the like.

The substituent term "$C_3$ to $C_7$ cycloalkyl" includes the cyclopropyl, cyclobutyl, cyclopentyl, cyclohexyl or cycloheptyl rings. The substituent term "$C_3$ to $C_7$ substituted cycloalkyl" indicates the above cycloalkyl rings substituted by a halogen, hydroxy, protected hydroxy, phenyl, substituted phenyl, heterocycle, substituted heterocycle, $C_1$ to C alkyl, $C_1$ to $C_4$ alkoxy, carboxy, protected carboxy, amino, or protected amino.

The substituent term "$C_3$ to $C_7$ cycloalkenyl" indicates a 1,2, or 3-cyclopentenyl ring, a 1,2,3 or 4-cyclohexenyl ring or a 1,2,3,4 or 5-cycloheptenyl ring, while the term "substituted $C_3$ to $C_7$ cycloalkenyl" denotes the above $C_3$ to $C_7$ cycloalkenyl rings substituted by a $C_1$ to $C_{10}$ alkyl radical, halogen, hydroxy, protected hydroxy, $C_1$ to $C_4$ alkoxy, carboxy, protected carboxy, amino, or protected amino.

The term "heterocyclic ring" or "heterocycle" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred. Preferred heterocyclic rings include pyridino, pyrimidino, and pyrazino, furano, thiofurano and imidazolyl rings. The heterocycles can be substituted or unsubstituted as, for example, with such substituents as those described in relation to substituted phenyl or substituted naphthyl.

The term "$C_7$ to $C_{16}$ phenylalkyl" denotes a $C_1$ to $C_{10}$ alkyl group substituted at any position by a phenyl ring. Examples of such a group include benzyl, 2-phenylethyl, 3-phenyl-(n-prop-1-yl), 4-phenyl-(-hex-1-yl), 3-phenyl-(n-am-2-yl), 3-phenyl-(sec-butyl), and the like. A preferred group is the benzyl group.

The term "$C_7$ to $C_{16}$ substituted phenylalkyl" denotes a $C_7$ to $C_{16}$ arylalkyl group substituted on the $C_1$ to $C_{10}$ alkyl portion with one or more, and preferably one or two, groups chosen from halogen, hydroxy, protected hydroxy, keto, $C_2$ to $C_3$ cyclic ketal, phenyl, amino, protected amino, $C_1$ to $C_7$ acyloxy, nitro, carboxy, protected carboxy, carbamoyl, carbamoyloxy, cyano, N-(methylsulfonylamino) or $C_1$ to $C_4$ alkoxy; and/or the phenyl group may be substituted with 1 or 2 groups chosen from halogen, hydroxy, protected hydroxy, nitro, $C_1$ to $C_{10}$ alkyl, $C_1$ to $C_6$ substituted alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, amino, (monosubstituted)amino, (disubstituted)amino, fluorenylmethyloxycarbonylamino, a N-(methylsulfonylamino) group, $C_1$ to $C_7$ acyl, or a phenyl group, substituted or unsubstituted, for a resulting biphenyl group. When either the $C_1$ to $C_{10}$ alkyl portion or the phenyl portion or both are mono- or di-substituted the substituents can be the same or different.

Examples of the term "$C_7$ to $C_{16}$ substituted phenylalkyl" include groups such as 2-phenyl-1-chloroethyl, 2-(4-methoxyphenyl)eth-1-yl, 2,6-dihydroxy-4-phenyl(n-hex-2-yl), 5-cyano-3-methoxy-2-phenyl(n-pent-3-yl), 3-(2,6-dimethylphenyl)n-prop-1-yl, 4-chloro-3-aminobenzyl, 6-(4-methoxyphenyl)-3-carboxy(n-hex-1-yl), 5-(4-aminomethyl-phenyl)-3-(aminomethyl) (n-pent-2-yl), 5-phenyl-3-keto-(n-pent-1-yl), 4-(4-aminophenyl)-4-(1,4-oxetanyl) (n-but-1-yl), and the like.

The term "$C_7$ to $C_{16}$ phenylalkenyl" denotes a $C_1$ to $C_{10}$ alkenyl group substituted at any position by a phenyl ring. The term "$C_7$ to $C_{16}$ substituted phenylalkenyl" denotes a $C_7$ to $C_{16}$ arylalkyl group substituted on the $C_1$ to $C_{10}$ alkenyl portion. Substituents can be the same as those as defined above in relation to $C_7$ to $C_{16}$ phenylalkyl and $C_7$ to $C_{16}$ substituted phenylalkyl. A preferred $C_7$ to $C_{16}$ substituted phenylalkenyl is 3-(4-nitrophenyl)-2-propenyl.

The term "substituted phenyl" specifies a phenyl group substituted with one or more, and preferably one or two, moieties chosen from the groups consisting of halogen, hydroxy, protected hydroxy, cyano, nitro, $C_1$ to $C_{10}$ alkyl, $C_1$ to $C_{10}$ substituted alkyl, $C_1$ to $C_4$ alkoxy, carboxy, protected carboxy, carboxymethyl, protected carboxymethyl, hydroxymethyl, protected hydroxymethyl, amino, protected amino, (monosubstituted)amino, protected (monosubstituted) amino, (disubstituted) amino, trifluoromethyl, N-(methylsulfonylamino), or phenyl, substituted or unsubstituted, such that, for example, a biphenyl results.

Examples of the term "substituted phenyl" includes a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or di(hydroxy)phenyl groups such as 4-hydroxyphenyl, 3-hydroxyphenyl, 2,4-dihydroxyphenyl, the protected-hydroxy derivatives thereof and the like; a nitrophenyl group such as 3-or 4-nitrophenyl; a cyanophenyl group for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-prop-1-yl)phenyl and the like; a mono or di(alkoxyl)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl, 3-(4-methylphenoxy)phenyl, and the like,; 3-or 4-trifluoromethylphenyl; a mono- or dicarboxyphenyl or (protected carboxy)phenyl group such as 4-carboxyphenyl or 2,4-di(protected carboxy)phenyl; a mono-or di(hydroxymethyl)phenyl or (protected hydroxymethyl) phenyl such as 3-(protected hydroxymethyl)phenyl or 3,4-di(hydroxymethyl)phenyl; a mono- or di(aminomethyl) phenyl or (protected aminomethyl)phenyl such as 2-(aminomethyl)phenyl or 2,4-(protected aminomethyl) phenyl; or a mono- or di(N-(methylsulfonylamino))phenyl such as 3-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy 4-chlorophenyl and the like.

The term "substituted benzyl" means a benzyl group substituted with one or more, and preferably one or two, moieties chosen from the same groups as provided with reference to "substituted phenyl." Examples of substituted benzyl include 4-bromobenzyl, 4-chlorobenzyl, 4-fluorobenzyl, 4-ethoxybenzyl, 4-hydroxybenzyl, 4-iodobenzyl, and the like.

The term "substituted naphthyl" specifies a naphthyl group substituted with one or more, and preferably one or two, moieties chosen from the groups consisting of halogen, hydroxy, protected hydroxy, cyano, nitro, $C_1$ to $C_{10}$ alkyl, $C_1$ to $C_4$ alkoxy, carboxy, protected carboxy, carboxymethyl, protected carboxymethyl, hydroxymethyl, protected hydroxymethyl, amino, protected amino,(monosubstituted) amino, protected (monosubstituted) amino, (disubstituted) amino trifluoromethyl or N-(methylsulfonylamino). Examples of substituted naphthyl include 2-(methoxy)-naphthyl and 4-(methoxy)naphthyl.

The term "naphthylmethyl" means a naphthyl group substituted with a methyl at the one or two position. "Substituted naphthylmethyl" specifies a naphthylmethyl substituted with one or more, and preferably one or two, moieties chosen from those groups as provided with reference to "substituted naphthyl" above. Examples of substituted naphthylmethyl include 4-4-hydroxynaphthylmethyl, 4-iodonaphthylmethyl, and the like.

The term "substituted indolyl" specifies a indolyl group substituted, either at the nitrogen or carbon, or both, with one or more, and preferably one or two, moieties chosen from the groups consisting of halogen, hydroxy, protected hydroxy, cyano, nitro, $C_1$ to $C_{10}$ alkyl, $C_1$ to $C_{10}$ substituted alkyl, $C_1$ to $C_{10}$ alkenyl, $C_7$ to $C_{16}$ phenylalkyl, $C_7$ to $C_{16}$ substituted phenylalkyl, $C_1$ to $C_6$ alkoxy, carboxy, protected carboxy, carboxymethyl, protected carboxymethyl, hydroxymethyl, protected hydroxymethyl, amino, protected amino, monosubstituted amino, or disubstituted amino.

Examples of the term "substituted indolyl" includes such groups as 6-fluoro, 5-fluoro, 5-bromo, 5-hydroxy, 5-methyl, 6-methyl, 7-methyl, 1-methyl, 1-ethyl, 1-benzyl, 1-napth-2-ylmethyl, and the like. An example of a disubstituted indolyl is 1-methyl-5-methyl indolyl.

The terms "halo" and "halogen" refer to the fluoro, chloro, bromo or iodo groups.

The term "(monosubstituted)amino" refers to an amino group with one substituent chosen from the groups consisting of phenyl, substituted phenyl, $C_1$ to $C_{10}$ alkyl, and $C_7$ to $C_{16}$ arylalkyl, wherein the latter three substituent terms are as defined above. The (monosubstituted)amino can additionally have an amino-protecting group as encompassed by the term "protected (monosubstituted)amino."

The terms "(disubstituted)amino" and "(trisubstituted) amino" refer to amino groups with two and three substituents, respectively chosen from the group consisting of phenyl, substituted phenyl, $C_1$ to $C_{10}$ alkyl, and $C_7$ to $C_{16}$ arylalkyl wherein the latter three substituent terms are as described above. The substituents can be the same or different.

The term "substituted carbamoyl" as used herein means the amino group of the aminocarbonyl is mono- or di-substituted with those same substituents as described above in relation to (monosubstituted)amino and (disubstituted)amino. A specific example is dimethylcarbamoyl.

The terms "(monosubstituted)guanidino," "(disubstituted)guanidino," and "(trisubstituted)guanidino" are where the guanidino groups is substituted with one, two, or three substituents, respectively. The substituents can be any of those as defined above in relation to (monosubstituted)amino and (disubstituted)amino and, where more than one substituent is present, the substituents can be the same or different.

The term "amino-protecting group" as used herein refers to substituents of the amino group commonly employed to block or protect the amino functionality while reacting other functional groups on the amine component. The term "protected (monosubstituted)amino" means there is an amino-protecting group on the monosubstituted amino nitrogen atom. In addition, the term "protected carboxamide"means there is an amino-protecting group replacing the proton so that there is no N-alkylation. Examples of such amino-protecting groups include the formyl ("For") group, the trityl group (Trt), the phthalimido group, the trichloroacetyl group, the chloroacetyl, bromoacetyl, and iodoacetyl groups, urethane-type blocking groups, such as t-butoxycarbonyl ("Boc"), 2-(4-biphenylyl)propyl(2)oxycarbonyl ("Bpoc"), 2-phenylpropyl(2)oxycarbonyl ("Poc"), 2-(4-xenyl)isopropoxycarbonyl, 1,1-diphenylethyl(1)-oxycarbonyl, 1,1-diphenylpropyl(1)oxycarbonyl, 2-(3,5-dimethoxyphenyl)propyl(2)oxycarbonyl ("Ddz"), 2-(p-toluyl)propyl(2)oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)-ethoxycarbonyl, 9-fluoroenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benz-isoxalylmethoxycarbonyl, 4-acetoxybenzyloxycarbonyl, 2,2,2-trichloroethoxycarbonyl, 2-ethynyl(2)propoxy-carbonyl, cyclopropylmethoxycarbonyl, isobornyl-oxycarbonyl, 1-piperidyloxycarbonyl, benzyloxycarbonyl ("Z"), 4-phenylbenzyloxycarbonyl, 2-methylbenzyloxy-carbonyl, α2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl, and the like; the benzoylmethylsulfonyl group, dithiasuccinoyl ("Dts"), the 2-(nitro)phenylsulfenyl group ("Nps"), the diphenyl-phosphine oxide group, and like amino-protecting groups. The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc and Fmoc. Further examples of amino-protecting groups embraced to by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rockford, Ill., 1984, each of which is incorporated herein by reference. The related term "protected amino" defines an amino group substituted with an amino-protecting group discussed above.

The term "substituted carboxy" as used herein refers to one of the ester derivatives of the carboxylic acid group, and denotes such radicals as methyl ester and ethyl ester. Substituted carboxy includes "protected carboxy," which refers to a carboxy group substituted with a carboxy-protecting group employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylprop-2-yl, trimethylsilyl, t-butyldimethylsilyl, 2,2,2-trichloroethyl, β-(trimethylsilyl)ethyl, β-(di(n-butyl) methylsilyl)ethyl, p-toluenesulfonylethyl, 4-nitrobenzyl-sulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in E. Haslam, "Protective Groups in Organic Chemistry," J. G. W. McOmie, Ed., Plenum Press, New York, N.Y., 1973, Chapter 5, and T. W. Greene and P. G. M. Wuts, "Protective Groups in Organic Synthesis," 2nd ed., John Wiley and Sons, New York, N.Y., 1991, Chapter 5, each of which is incorporated herein by reference The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl and 2,2,2-trichloroethoxycarbonyl groups and the like. The species of hydroxy-protecting groups is not critical so long as the derivatized hydroxyl group is stable to the conditions of subsequent reaction(s) and can be removed at the appropriate point without disrupting the remainder of the hydantoin. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

The substituent term "$C_1$ to $C_4$ alkylthio" refers to sulfide groups such as methylthio, ethylthio, n-propylthio, iso-propylthio, n-butylthio, t-butylthio and like groups.

The substituent term "$C_1$ to $C_4$ alkylsulfoxide" indicates sulfoxide groups such as methylsulfoxide, ethylsulfoxide, n-propylsulfoxide, iso-propylsulfoxide, n-butylsulfoxide, sec-butylsulfoxide, and the like.

The term "$C_1$ to $C_4$ alkylsulfonyl" encompasses groups such as methylsulfonyl, ethylsulfonyl, n-propylsulfonyl, iso-propylsulfonyl, n-butylsulfonyl, t-butylsulfonyl, and the like.

Phenylthio, phenyl sulfoxide, and phenylsulfonyl compounds are known in the art and these terms have their art recognized definition. By "substituted phenylthio," "substituted phenyl sulfoxide," and "substituted phenylsulfonyl" is meant that the phenyl can be substituted as described above in relation to "substituted phenyl."

The substituent terms "cyclic $C_2$ to $C_{10}$ alkylene," "substituted cyclic $C_2$ to $C_{10}$ alkylene," "cyclic $C_2$ to $C_{10}$ heteroalkylene," and "substituted cyclic $C_2$ to $C_{10}$ heteroalkylene," defines such a cyclic group bonded ("fused") to the phenyl radical. The cyclic group may be saturated or contain one or two double bonds. Furthermore, the cyclic group may have one or two methylene groups replaced by one or two oxygen, nitrogen or sulfur atoms.

The cyclic alkylene or heteroalkylene group may be substituted once or twice by substituents selected from the group consisting of the following moieties: hydroxy, protected hydroxy, carboxy, protected carboxy, keto, ketal, $C_1$ to $C_4$ alkoxycarbonyl, formyl, $C_2$ to $C_4$ alkanoyl, $C_1$ to $C_{10}$ alkyl, carbamoyl, $C_1$ to $C_4$ alkoxy, $C_1$ to $C_4$ alkylthio, $C_1$ to $C_4$ alkylsulfoxide, $C_1$ to $C_4$ alkylsulfonyl, halo, amino, protected amino, hydroxymethyl or a protected hydroxymethyl.

The cyclic alkylene or heteroalkylene group fused onto the benzene radical can contain two to ten ring members, but it preferably contains four to six members. Examples of such saturated cyclic groups are when the resultant bicyclic ring system is 2,3-dihydroindanyl and a tetralin ring. When the cyclic groups are unsaturated, examples occur when the resultant bicyclic ring system is a naphthyl ring or indanyl. An example of a cyclic group which can be fused to a phenyl radical which has two oxygen atoms and which is fully saturated is dioxanyl. Examples of fused cyclic groups which each contain one oxygen atom and one or two double bonds are when the phenyl ring is fused to a furo, pyrano, dihydrofurano, or dihydropyrano ring. Examples of cyclic groups which each have one nitrogen atom and contain one or two double more double bonds are when the phenyl is fused to a pyridino or pyrano ring. An example of a fused ring system having one nitrogen and two phenyl radicals is a carbozoyl group. Examples of cyclic groups which each have one sulfur atom and contain one or two double bonds are when the phenyl is fused to a thieno, thiopyrano, dihydrothieno or dihydrothiopyrano ring. Examples of cyclic groups which contain two heteroatoms selected from sulfur and nitrogen and one or two double bonds are when the phenyl ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring.

One or more of the hydantoins or thiohydantoins within a given library may be present as a pharmaceutically acceptable salt. The term "pharmaceutically-acceptable salt" encompasses those salts that form with the carboxylate anions and include salts formed with the organic and inorganic cations discussed below. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counterions for the carboxylate anion of a carboxylate salt. The counter-ions are chosen from the alkali and alkaline earth metals, (such as lithium, sodium, potassium, barium and calcium); ammonium; and the organic cations (such as dibenzylammonium, benzylammonium, 2-hydroxyethylammonium, bis(2-hydroxyethyl)ammonium, phenylethylbenzylammonium, dibebenzylethylenediammonium, and like cations). Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. A preferred cation for the carboxylate anion is the sodium cation.

The compounds of the above Formula can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more hydantoins or thiohydantoins can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the $\alpha$-($C_1$ to $C_4$) alkoxyethyl groups, for example methoxyethyl, ethoxyethyl, propxyethyl, iso-propoxyethyl, and the like; the 2-oxo-1,3-diosolen-4-ylmethyl groups, such as 5-methyl-2-oxo-1,3-dioxolen-4-ylmethyl, 5-phenyl-2-oxo-1,3-dioxolen-4-ylmethyl, and the like; the $C_1$ to $C_3$ alkylthiomethyl groups, for example methylthiomethyl, ethylthiomethyl, isopropylthiomethyl, and the like; the acyloxymethyl groups, for example pivaloyloxymethyl, pivaloyloxyethyl, $\alpha$-acetoxymethyl, and the like; the ethoxycarbonyl-1-methyl group; the $\alpha$-acetoxyethyl; the 3-phthalidyl or 5,6-dimethylphthalidyl groups; the 1-($C_1$ to $C_4$ alkyloxycarbonyloxy)ethyl groups such as the 1-(ethoxycarbonyloxy)ethyl group; and the 1-($C_1$ to $C_4$ alkylaminocarbonyloxy)ethyl groups such as the 1-(methylaminocarbonyloxy)ethyl group.

As used herein, a chemical or combinatorial "library" is an intentionally created collection of differing molecules which can be prepared by the synthetic means provided below or otherwise and screened for biological activity in a variety of formats (e.g., libraries of soluble molecules, libraries of compounds attached to resin beads, silica chips or other solid supports). The libraries can be screened in any variety of assays, such as those detailed below as well as others useful for assessing the biological activity of hydantoins and thiohydantoins. The libraries will generally have at least one active compound and are generally prepared in such that the compounds are in equimolar quantities.

"Combinatorial chemistry" or "combinatorial synthesis" refers to the parallel synthesis of diverse compounds by sequential addition of reagents which leads to the generation of large chemical libraries having molecular diversity. Combinatorial chemistry, therefore, involves the systematic and repetitive, covalent connection of a set of different "building blocks" of varying structures to yield large arrays of diverse molecular entities.

Because libraries can be screened while still bound to the solid-phase resin, as described above, embodiments of the invention include libraries bound to an amino resin (Y=N and Z=amino resin) or hydroxy resin (Y=O and Z=hydroxy resin). In the case when Y is nitrogen, the compounds in such libraries would be resin-bound through the amine attached to $R^2$ (p=1) in the above Formula and as exemplified in FIG. 1. In the case when Y is oxygen, the compounds of such library would be resin-bound through the oxygen and $R^2$ would be absent (p=zero). As would be appreciated to those of skill in the art, the nitrogen and oxygen atoms at Y are functions supplied by their respective resins, which will be cleaved from the resin and retained with the compounds of the subject invention. By "amino resin" and "hydroxy resin" is meant polymers functionalized with amino or hydroxy groups, respectively, such as 4-methylbenzhydrylamine (MBHA), 4-methylbenzhydrylamine-copoly(styrene-1% divinylbenzene), 4-(oxymethyl)-phenylacetamido methyl (Pam), 4-(oxymethyl)-phenylacetamido methyl-copoly (styrene-1% divinylbenzene), and others well known in the art. Collectively, these resins are termed "functionalized resins." Once the compounds are cleaved from the resins, Z is hydrogen.

As will be described in further detail, three libraries were prepared, two hydantoin libraries (X=O), one non-alkylated having $R^2$, $R^4$ and $R^5$ each as hydrogen and another alkylated having $R^2$ as methyl, ethyl, allyl, and benzyl, $R^4$ as hydrogen, methyl and benzyl, and $R^5$ as hydrogen. One non-alkylated thiohydantoin library (X=S), was prepared having $R^2$, $R^4$ and $R^5$ each as hydrogen. For these three libraries, the $R^1$ and $R^3$ positions varied as described above and, in further detail, below. It should be appreciated, however, that such libraries can comprise several smaller "sub-libraries" or sets of mixtures of compounds, depending on the format of preparation and the varying R groups. Sublibraries are described in further detail below.

The hydantoin and thiohydantoin libraries and compounds of Formula I can be prepared according to the general Reaction Scheme I in FIG. 1. The libraries were prepared using solid-phase techniques. The solid-phase resin, here p-methylbenzhydrylamine resin (MBHA), is indicated in FIG. 1 by the large circle and dash. As described above, other resins such as hydroxy resins can alternatively be used.

With reference to Reaction Scheme I, following addition of a protected amino acid (having side chain $R^1$ with m=0 and n=0 except when $R^1$ is derived from $\beta$-alanine, m=1; $\gamma$-aminobutyric acid, m=2; $\delta$-ornithine, n=3; $\epsilon$-lysine, n=4; $\epsilon$-aminocaproic acid, m=3; 7-aminoheptanoic acid, m=5; $\beta$-aspartic acid, m=1; isoasparagine, m=1; $\gamma$-glutamic acid, m=2; or isoglutamine, m=2) to the resin, the amine is deprotected.

The next key step in the synthetic process, as shown in FIG. 1, is an optional alkylation, which can be performed to introduce a functionality other than hydrogen at $R^2$. Following tritylation of the amine, the amide linked to the solid support is selectively N-alkylated (illustrated in FIG. 1). The N-alkylation can be performed using lithium t-butoxide in THF, followed by addition of the alkylating agent in DMSO. The alkylating agents are those which include the $R^2$ groups described above, derivatized with, for example, a bromo, iodo, triflate or methylsulfonate group. Other alkylating derivatives of the group $R^2$ are well known. Preferably the alkylating agent is methyl iodide, ethyl bromide, allyl bromide, or benzyl bromide. This method of N-alkylation is known and has been used for the synthesis of soluble peptidomimetic combinatorial libraries through successive or exhaustive amide alkylation as described, for example, in Dörner et al. *Bioorg. & Med. Chem.*, 4:709 (1996) and Ostresh et al. *Proc. Nat, Acad, Sci.*, 91:11138 (1994), both of which are incorporated herein by reference. This method has been used to generate diverse chemical libraries using the "libraries from libraries" concept as described, for instance, in Ostresh et al. *Proc. Nat. Acad. Sci.*, 91:11138 (1994), incorporated herein by reference. It should be appreciated from the above described embodiments of $R^1$ that some of the amino acids are modified during the synthesis, which is explained in further detail below. The trityl ("Trt") protecting group is removed with 2% TFA in DCM.

Again with reference to Reaction Scheme I in FIG. 1, if N-alkylation is performed, the Trt protecting group is removed with 2% TFA in DCM, and a second protected amino acid (having side chain $R^3$) is added using traditional solid phase peptide chemistry. If a functionality other than hydrogen was introduced at $R^2$ during the previously described alkylation, Boc-amino acids (or other protected amino acids with acid labile $N^\alpha$-protecting groups) should not be used because of the increased lability of the resulting secondary amides to acidic cleavage.

The cyclizations to obtain the five-member ring hydantoins and thiohydantoins were performed using triphosgene and thiocarbonyldiimidazole, respectively, as described in the ensuing Examples. Alternatively, the cyclization step can carried out using phosgene or thiophosgene by the same procedures described for triphosgene. Additionally, carbonyldiimidazole can be used following the same conditions as those described below for thiocarbonyldiimidazole.

Following cyclization, if the first amino acid was not alkylated ($R^2$ is hydrogen), the side chains of the amino acids incorporated into the hydantoins and thiohydantoins can be deprotected using the "low HF" deprotection procedure of Tam, et al. *Int. J. Pep, Prot. Res.*, 21:57 (1983), which is incorporated herein by reference.

The next key step in the synthesis, as shown in FIG. 1, is the optional selective N-alkylation of the hydantoin or thiohydantoin ring. The N-alkylation can be performed using sodium cyclopentadienylide in THF, followed by addition of the alkylating agent in DMSO. The alkylating agents are those which include the $R^4$ groups described above, derivatized with, for example, a bromo, iodo, triflate or methylsulfonate group. Other alkylating derivatives of the group $R^4$ are well known. Preferably the alkylating agent is methyl iodide, or benzyl bromide. The method of N-alkylation is similar to that described above. Due to the lower basicity of sodium cyclopentadienylide in THF compared to lithium t-butoxide in THF, this alkylation method is selective for the active nitrogen in the hydantoin ring. It should be appreciated from the above described embodiments of $R^3$ that some of the amino acids are modified during the synthesis, which is explained in further detail below.

The next key step in the synthetic process, as shown in FIG. 1, is an optional C-alkylation, which can be performed to introduce a functionality other than hydrogen at $R^5$. The C-alkylation can be performed using lithium t-butoxide in THF, followed by addition of the alkylating agent in DMSO. The alkylating agents are those which include the $R^5$ groups described above, derivatized with, for example, a bromo, iodo, triflate or methylsulfonate group. Other alkylating derivatives of the group $R^5$ are well known. Preferably the alkylating agent is methyl iodide, or benzyl bromide. This method of C-alkylation is similar to that described above to introduce a functionality other than hydrogen at $R^2$. Due to the basicity of lithium t-butoxide in THF, this alkylation is non-selective. Therefore, if either or both $R^2$ and $R^4$ are hydrogens, the respective nitrogens will also be alkylated. If $R^5$ is to be alkylated and one or both of $R^2$ and $R^4$ are to remain a hydrogen atom, these unsubstituted nitrogen(s) are first reacted with a protecting group inert to the alkylation conditions for $R^5$. Such a protecting group would be, for example, the dimethoxybenzyl group, put in place by alkylating one or both unsubstituted nitrogens under known conditions with dimethoxyenzyl bromide. This protecting group is removed by known methods after the alkylation with the $R^5$ group.

Any variety of amino acids can be used with the present invention as described above to generate a vast array of hydantoins and thiohydantoins with different $R^1$, and $R^3$ groups. For example, as described in the ensuing Examples, ninety-two different first amino acids (Boc protected) were coupled to the resin, which amino acids contain $R^1$. The ninety-two amino acids included Ala, ala, β-Ala, Cha, cha, Nal, nal, Pya, pya, Tha, tha, Cys(MeoBzl), cys(MeoBzl), Asp(Bzl), asp(Bzl), Asp(Fm), β-Asp(Fm), β-Asp(Bzl), Glu (Bzl), glu(Bzl), Glu(Fm), γ-Glu(Bzl), Phe, phe, pNH$_2$-Phe (Fmoc), pNH$_2$-phe(Fmoc), p-benzoyl-phe, pCl-Phe, pCl-phe, pF-Phe, pF-phe, pI-Phe, pI-phe, pNO$_2$-Phe, pNO$_2$-phe, Gly, tBu-Gly, Chg, Phg, phg, His(Dnp), his(Dnp), His(tos), Ile, ile, Lys(Clz), lys(Clz), Lys(Fmoc), lys(Fmoc), Lys(Ac), ε-Lys(Fmoc), ε-lys(Clz), Leu, leu, Nle, nle, Met(O), Met (O$_2$), Asn, asn, isoAsn, Orn(Cbz), Orn(Fmoc), δ-orn(Cbz), Gln, gln, isoGln, Arg(Tos), arg(Tos), Ser(Bzl), ser(Bzl), Thr(Bzl), Val, val, Nve, nve, Trp(CHO), trp(CHO), Trp, trp, Tyr(Brz), tyr(Brz), Tyr(2,6-diClBzl), tyr(2,6-diClBzl), Tyr (Et), tyr(Et), α-Aba, γ-Aba, ε-Aca, 7-Aha, and α-Aib.

Seventy-nine Boc-protected and forty-five Fmoc-protected amino acids were coupled as the second amino acids, thereby providing the various $R^3$ groups. The seventy-nine Boc-protected amino acids included Ala, ala, Cha, cha, Nal, nal, Pya, pya, Tha, tha, Cys(MeoBzl), cys(MeoBzl), Asp(Bzl), asp(Bzl), Asp(Fm), Glu(Bzl), glu(Bzl), Phe, phe, pNH$_2$-Phe(Fmoc), pNH$_2$-phe(Fmoc), p-benzoyl-phe, pCl-Phe, pCl-phe, pF-Phe, pF-phe, pI-Phe, pI-phe, pNO$_2$-Phe, pNO$_2$-phe, Gly, Chg, tBu-Gly, Phg, phg, His(Dnp), his (Dnp), His(Tos), his(Tos), Ile, ile, Lys(Clz), lys(Clz), Lys (Fmoc), lys(Fmoc), Lys(Ac), Leu, leu, Nle, nle, Met(O), Met (O$_2$) , Asn, asn, Orn(Cbz), Orn(Fmoc), Gln, gln, Arg(Tos), arg(Tos), Ser(Bzl), ser(Bzl), Thr(Bzl), thr(Bzl), Val, val, Trp(CHO), trp(CHO), Trp, trp, Tyr(Brz), tyr(Brz), Tyr(Et), tyr(Et), α-Aba, and α-Aib. The forty-five Fmoc-protected amino acids included Ala, ala, Cha, cha, Nal, nal, Pya, Glu(tBu), glu(tBu), Phe, phe, pCl-Phe, pcl-phe, Gly, Phg, Ile, ile, Lys(Boc), lys(Boc), Leu, leu, Nel, nle, Met(O), Asn(Trt), asn(Trt), Gln(Trt), gln(Trt), Arg(Pmc), arg(Pmc), Ser(tBu), ser(tBu), Thr(tBu), thr(tBu), Val, val, Nve, nve, Trp(Boc), trp(Boc), Trp, trp, Tyr(tBu), tyr(tBu), and Tyr (Brz).

As used herein, abbreviations for the various amino acid side-chain protecting groups are as follows: "Fmoc" for fluorenylmethyloxycarbonyl, "Boc" for tert-butoxycarbonyl, "MeoBzl" for p-methoxybenzyl, "Bzl" for benzyl, "Fm" for fluorenylmethyl, "Dnp" for 2,4-dinitrophenyl, "Tos" for tosyl, "Clz" for 2-chlorobenzyloxycarbonyl, "O" for sulfoxide, "O$_2$" for sulfone, "Cbz" for benzyloxycarbonyl, "CHO" for formyl, "Brz" for 2-bromobenzyloxycarbonyl, "2,6-diClBzl" for 2,6-dichlorobenzyl, "Et" for ethyl, "Ac" for acetyl, "tBu" for tert-butyl, "Trt" for trityl, and "Pmc" for 2,2,5,7,8-pentamethylchroman-6-sulfonyl. These abbreviations and any others used herein are those which are commonly known and used in the field. Moreover, also as is commonly practiced in the field and with reference to the amino acid nomenclature, all lower case lettering herein means the D-form of the amino acid as opposed to the L-form. Other nomenclature and abbreviations used herein for amino acids and derivatives thereof, as well as their respective side chains are as follows:

TABLE 1

| AMINO ACID NAME | | SIDE CHAIN R (FOR $R^1$ AND $R^3$), m = 0 and n = 0 |
|---|---|---|
| FULL | CODE | except as noted |
| Alanine | Ala | $-CH_3$ |
| β-Alanine | β-Ala | $-H$, m = 1 |
| Cyclohexyl-alanine | Cha | $-CH_2-$cyclohexyl |
| 2-Naphthyl-alanine | Nal | $-CH_2-$naphthyl |
| 3-Pyridyl-alanine | Pya | $-CH_2-$pyridyl |
| 2-Thienyl-alanine | Tha | $-CH_2-$thienyl |
| Cysteine | Cys | $-CH_2SH$ |
| Aspartic acid | Asp | $-CH_2COOH$ |
| β-Aspartic acid | β-Asp | $-COOH$, m = 1 |
| Glutamic acid | Glu | $-CH_2CH_2COOH$ |
| γ-Glutamic acid | γ-Glu | $-COOH$, m = 2 |
| Phenyl-alanine | Phe | $-CH_2-$phenyl |
| p-amino-Phenyl-alanine | $pNH_2$-Phe | $-CH_2-$C$_6$H$_4-$NH$_2$ |
| p-benzoyl-Phenyl-alanine | p-benzoyl-Phe | $-CH_2-$C$_6$H$_4-$CO-C$_6$H$_5$ |
| p-chloro-Phenyl-alanine | pCl-Phe | $-CH_2-$C$_6$H$_4-$Cl |
| p-fluoro-Phenyl-alanine | pF-Phe | $-CH_2-$C$_6$H$_4-$F |
| p-iodo-Phenyl-alanine | pI-Phe | $-CH_2-$C$_6$H$_4-$I |
| p-nitro-Phenyl-alanine | $pNO_2$-Phe | $-CH_2-$C$_6$H$_4-$NO$_2$ |
| Glycine | Gly | $-H$ |
| t-butyl-Glycine | tBu-Gly | $-C(CH_3)_3$ |
| Cyclohexyl-glycine | Chg | cyclohexyl |
| Phenyl-glycine | Phg | phenyl |
| Histidine | His | $-CH_2-$imidazolyl |
| Isoleucine | Ile | $-CH(CH_3)CH_2CH_3$ |
| Lysine | Lys | $-(CH_2)_4NH_2$ |
| ε-Lys | ε-Lys | $-NH_2$, n = 4 |
| Leucine | Leu | $-CH_2CH(CH_3)_2$ |
| Norleucine | Nle | $-CH_2CH_2CH_2CH_3$ |
| Methionine | Met | $-CH_2CH_2SCH_3$ |
| Asparagine | Asn | $-CH_2CONH_2$ |
| Iso-asparagine | isoAsn | $-CONH_2$, m = 1 |
| Ornithine | Orn | $-(CH_2)_3NH_2$ |
| δ-Ornithine | δ-Orn | $-NH_2$, n = 3 |
| Glutamine | Gln | $-CH_2CH_2CONH_2$ |
| Isoglutamine | isoGln | $-CONH_2$, m = 2 |
| Arginine | Arg | $-CH_2CH_2CH_2NHC(NH)NH_2$ |
| Serine | Ser | $-CH_2OH$ |
| Threonine | Thr | $-CH(OH)CH_3$ |
| Valine | Val | $-CH(CH_3)CH_3$ |
| Norvaline | Nve | $-CH_2CH_2CH_3$ |
| Tryptophan | Trp | $-CH_2-$indolyl |
| Tyrosine | Tyr | $-CH_2-$C$_6$H$_4-$OH |
| α-amino-butyric acid | α-Aba | $-CH_2CH_3$ |
| γ-amino-butyric acid | γ-Aba | $-H$, m = 2 |
| ε-amino-caproic acid | ε-Aca | $-H$, m = 3 |
| 7-amino-heptanoic acid | 7-Aha | $-H$, m = 5 |

TABLE 1-continued

| AMINO ACID NAME | | SIDE CHAIN R (FOR $R^1$ AND $R^3$), m = 0 and n = 0 |
|---|---|---|
| FULL | CODE | except as noted |
| α-amino-isobutyric acid | α-Aib | $-(CH_3)_2$ |

As can be seen from the side chains exemplified in the above Table, m and n in Formula I in all preferred instances is 0, except where noted.

It should be appreciated from the above-described embodiments of $R^1$ and $R^{3,}$ as well as from the described reaction scheme, that some of the amino acid side chains are modified during the synthesis. For instance some of the $R^1$ and $R^3$ amino acid side chains are modified by the alkylation steps. Accordingly, with reference to the preferred embodiments of $R^1$ and $R^3$, they are described above and below, except in Table I, in their modified form.

The subject libraries are useful for rapidly preparing and screening a wide array of compounds and have utility in optimization and drug discovery programs. The libraries can be screened while still on the resin or after cleavage.

The nonsupport-bound library mixtures were screened in solution in radio-receptor inhibition assays and an antibacterial assay described in detail below. Deconvolution of highly active mixtures can then be carried out by iterative or positional scanning methods. These techniques, the iterative approach or the positional scanning approach, can be utilized for finding other active compounds within the libraries of the present invention using any one of the below-described assays or others well known in the art.

The iterative approach is well-known and is set forth in general in Houghten et al., Nature, 354, 84–86 (1991) and Dooley et al., Science. 266, 2019–2022 (1994), both of which are incorporated herein by reference. In the iterative approach, for example, sub-libraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various libraries as described, for example, in R. Houghten et al. PCT/US91/08694 and U.S. Pat. No. 5,556,762, both of which are incorporated herein by reference. The positional scanning approach is used as described below in the preparation and screening of the libraries. In the positional scanning approach sublibraries are made defining only one variable with each set of sublibraries- and all possible sublibraries with each single variable defined (and all other possibilities at all of the other variable positions) is made and tested. From the instant description one skilled in the art could synthesize libraries wherein 2 fixed positions are defined at a time. From the testing of each single-variable defined library, the optimum substituent at that position is determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Individual compounds and pharmaceutical compositions containing the new hydantoins and thiohydantoins, as well as methods of using the same are included within the scope of the present invention. The new hydantoin compounds of the present invention can be used for a variety of purposes and indications and as medicaments for such purposes and indications. As described, for instance, in Hanessian and Yang, *Tet. Lett.,* 37:5835 (1996), hydantoins are known to possess a wide range of biological activities, including anticonvulsant, antiarrhythmic and antidiabetic as well as herbicidal and fungicidal.

Moreover, as shown in Examples II, IV and VI, hydantoins and thiohydantoins of the present invention have antimicrobial activity. Thus the hydantoins of the present invention can be used to treat infections. The ability of the compounds to inhibit bacterial growth can be determined by methods well known in the art. An exemplary in vitro antimicrobial activity assay is described in Blondelle and Houghten, *Biochemistry* 30:4671–4678 (1991), which is incorporated herein by reference. In brief, Staphylococcus aureus ATCC 29213 (Rockville, Md.) is grown overnight at 37° C. in Mueller-Hinton broth, then re-inoculated and incubated at 37° C. to reach the exponential phase of bacterial growth (i.e., a final bacterial suspension containing $10^5$ to $5 \times 10^5$ colony-forming units/ml). The concentration of cells is established by plating 100 $\mu$l of the culture solution using serial dilutions (e.g., $10^{-2}, 10^{-3}$ and $10^{-4}$) onto solid agar plates. In 96-well tissue culture plates hydantoins, individual or in mixtures, are added to the bacterial suspension at concentrations derived from serial two-fold dilutions ranging from 1500 to 2.9 $\mu$g/ml. The plates are incubated overnight at 37° C. and the growth determined at each concentration by $OD_{620}$ nm. The $IC_{50}$ (the concentration necessary to inhibit 50% of the growth of the bacteria) can then be calculated.

Additional assays can be, and have been, used to test the biological activity of the instant hydantoins. One such assay is the competitive enzyme-linked immunoabsorbent assay (ELISA): The competitive ELISA method which can be used here is a modification of the direct ELISA technique described previously in Appel et al., *J. Immunol.* 144:976–983 (1990), which is incorporated herein by reference. It differs only in the MAb addition step. Briefly, multi-well microplates are coated with the antigenic peptide (Ac-GASPYPNLSNQQT-NH$_2$) at a concentration of 100 pmol/50 $\mu$l. After blocking, 25 $\mu$l of a 1.0 mg/ml solution of each hydantoin mixture of a synthetic combinatorial library (or individual hydantoin) is added, followed by MAb 125-10F3 (Appel et al., supra) (25 $\mu$l per well). The MAb is added at a fixed dilution in which the hydantoin in solution effectively competes for MAb binding with the antigenic peptide adsorbed to the plate. The remaining steps are the same as for direct ELISA. The concentration of hydantoin necessary to inhibit 50% of the MAb binding to the control peptide on the plate ($IC_{50}$) is determined by serial dilutions of the hydantoin.

Alternative screening can be, and has been, done with radio-receptor assays, as provided in Examples IV and VI.

These assays can be selective for any one of the $\mu$, K, or $\delta$ opiate receptors. Therefore, the compounds of the present invention are useful in vitro for the diagnosis of relevant opioid receptor subtypes, such as $\mu$, in the brain and other tissue samples. Similarly, the compounds can be used in vivo diagnostically to localize opioid receptor subtypes. The radio-receptor assays are also an indication of hydantoins' analgesic properties as described, for example, in Dooley et al., *Proc. Natl. Acad. Sci.,* 90:10811–10815 (1993). Additionally, such compounds can be tested in a $\sigma$ receptor assay. Ligands for the $\sigma$ receptor can be useful as antipsychotic agents, as described in Abou-Gharbia et al., *Annual Reports in Medicinal Chemistry,* 28:1–10 (1993).

The radio-receptor assay can be done as follows. Particulate membranes can be prepared using a modification of the method described in Pasternak et al., *Mol. Pharmacol.* 11:340–351 (1975), which is incorporated herein by reference. Rat brains frozen in liquid nitrogen can be obtained from Rockland (Gilbertsville, Pa.). The brains are thawed, the cerebella removed and the remaining tissue weighed. Each brain is individually homogenized in 40 ml Tris-HCl buffer (50 mM, pH 7.4, 4° C.) and centrifuged (Sorvall® RC5C SA-600: Du Pont, Wilmington, Del.) (16,000 rpm) for 10 mins. The pellets are resuspended in fresh Tris-HCl buffer and incubated at 37° C. for 40 mins. Following incubation, the suspensions are centrifuged as before, the resulting pellets resuspended in 100 volumes of Tris buffer and the suspensions combined. Membrane suspensions are prepared and used in the same day. Protein content of the crude homogenates generally range from 0.15–0.2 mg/ml as determined using the method described in M. M. Bradford, M. M., *Anal. Biochem.* 72:248–254 (1976), which is incorporated herein by reference.

Binding assays are carried out in polypropylene tubes, each tube containing 0.5 ml of membrane suspension. 8 nM of $^3$H- [D-Ala$^2$, Me-Phe$^4$, Gly-ol$^5$] enkephalin (DAMGO) (specific activity = 36 Ci/mmol, 160,000 cpm per tube; which can be obtained from Multiple Peptide Systems, San Diego, Calif., through NIDA drug distribution program 271-90-7302) and 80 $\mu$g/ml of hydantoin, individual or as a mixture and Tris-HCl buffer in a total volume of 0.65 ml. Assay tubes are incubated for 60 mins. at 25° C. The reaction is terminated by filtration through GF-B filters on a Tomtec harvester (Orange, Conn.). The filters are subsequently washed with 6 ml of Tris-HCl buffer, 4° C. Bound radioactivity is counted on a Pharmacia Biotech Betaplate Liquid Scintillation Counter (Piscataway, N.J.) and expressed in cpm. To determine inter- and intra-assay variation, standard curves in which $^3$H-DAMGO is incubated in the presence of a range of concentrations of unlabeled DAMGO (0.13–3900 nM) are generally included in each plate of each assay (a 96-well format). Competitive inhibition assays are performed as above using serial dilutions of the hydantoins, individually or in mixtures. IC$_{50}$ values (the concentration necessary to inhibit 50% of $^3$H-DAMGO binding) are then calculated. As opposed to this $\mu$ receptor selective assay, assays selective for K receptors can be carried out using [$^3$H]-U69,593 (3 nM, specific activity 62 Ci/mmol) as radioligand. Assays selective for $\delta$ opiate receptors can be carried out using tritiated DSLET ([D-Ser$^2$, D-Leu$^5$]-threonine-enkephalin) as radioligand. Similarly, assays for the $\sigma$ receptor assay are the same as the $\mu$ assay but use radiolabeled pentazocine as ligand.

As pharmaceutical compositions for treating infections, pain, or other indications known to be treatable by hydantoins or thiohydantoins, the hydantoin compounds of the present invention are generally in a pharmaceutical composition so as to be administered to a subject at dosage levels of from 0.7 to 7000 mg per day, and preferably 1 to 500 mg per day, for a normal human adult of approximately 70 kg of body weight, this translates into a dosage of from 0.01 to 100 mg/kg of body weight per day. The specific dosages employed, however, can be varied depending upon the requirements of the patient, the severity of the condition being treated, and the activity of the compound being employed. The determination of optimum dosages for a particular situation is within the skill of the art.

For preparing pharmaceutical compositions containing compounds of the invention, inert, pharmaceutically acceptable carriers are used. The pharmaceutical carrier can be either solid or liquid. Solid form preparations include, for example, powders, tablets, dispersible granules, capsules, cachets, and suppositories.

A solid carrier can be one or more substances which can also act as diluents, flavoring agents, solubilizers, lubricants, suspending agents, binders, or tablet disintegrating agents; it can also be an encapsulating material.

In powders, the carrier is generally a finely divided solid which is in a mixture with the finely divided active component. In tablets, the active compound is mixed with the carrier having the necessary binding properties in suitable proportions and compacted in the shape and size desired.

For preparing pharmaceutical composition in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter and the like.

The pharmaceutical compositions can include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid pharmaceutical compositions include, for example, solutions suitable for oral or parenteral administration, or suspensions, and emulsions suitable for oral administration. Sterile water solutions of the active component or sterile solutions of the active component in solvents comprising water, ethanol, or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical composition is in unit dosage form. In such form, the composition is divided into unit doses containing appropriate quantities of the active hydantoin. The unit dosage form can be a packaged preparation, the package containing discrete quantities of the preparation, for example, packeted tablets, capsules, and powders in vials or ampules. The unit dosage form can also be a capsule, cachet, or tablet itself, or it can be the appropriate number of any of these packaged forms.

The following Examples are intended to illustrate but not limit the present invention.

INTRODUCTION

When using either the iterative or positional scanning approach to the synthesis of the instant libraries, it is necessary at some point to expose either the solid phase alone or the solid phase bound to one or more amino acids, cyclized or uncyclized, either substituted or unsubstituted at $R^2$, $R^4$, or $R^5$, to a mixture of reactive subunits. Such subunits can be the first or second amino acid, or an alkylating agent for $R^2$, $R^4$, or $R^5$. As each individual subunit in the mixture may react at varying rates with the solid phase or the molecule bound to the solid phase, it is advantageous to know the relative reaction rate of each reactive subunit. Once such relative rates are known, the concentration of each reactive subunit can be adjusted accordingly in order to have approximately equimolar amounts of each reactive subunit couple with either the bare solid support or the molecule bound to the support. (For a further discussion of this point, see J. M. Ostresh et al., *Biopolymers*, 34:1661–1689 (1994), herein incorporated by reference).

The theory underpinning the methodology for determining the relative reaction rates used by Ostresh et al. in the above-mentioned *Biopolymers* article is set forth below.

Assuming that a large excess of the amino acid to be reacted with the Peptide which in turn is bound to the solid support is used, then the rate of such a reaction for amino acid 1 and amino acid 2 is expressed in Equations (1) and (2) below, respectively:

$$[\text{Peptide}-AA_1] = k_{AA-1} \times [AA_1] \quad (1)$$

wherein:

"Peptide"=Ala-Phe-Leu-;

$AA_1$=baseline amino acid; and $k_{AA-1}$=reaction constant of $AA_1$ with Peptide.

$$[\text{Peptide}-AA_2] = k_{AA-2} \times [AA_2] \quad (2)$$

wherein:

"Peptide"=Ala-Phe-Leu-;

$AA_2$=amino acid whose reaction rate with Peptide is to be compared to $AA_1$; and $k_{AA-2}$=reaction rate of $AA_2$ with the Peptide.

If $k_{AA-1}$ and $k_{AA-2}$ are different, then for any given period of time, more of the AA with the slower rate must be added to the mixture of reactive subunits so that the Peptide attached to the solid support will have reacted at that step with approximately equal amounts of $AA_1$ and $AA_2$. Thus, only relative rates are of importance, and can be determined using the following equations:

$$\frac{k_{AA-1}}{k_{AA-2}} = \frac{[\text{peptide}-AA_1] \times [AA_2]}{[\text{peptide}-AA_2] \times [AA_1]} \quad (3)$$

In order to simplify the calculations, a ten fold molar excess of both $AA_1$ and $AA_2$ are used in experiments coupling the AA in question to the solid support "Peptide"; allowing Equation 3 to be simplified to Equation 4:

$$\frac{k_{AA-1}}{k_{AA-2}} = \frac{[\text{peptide}-AA_1]}{[\text{peptide}-AA_2]} \quad (4)$$

on the assumption that $[AA_1]=[AA_2]$.

In order to determine the proper ratio of concentrations of $AA_1$ and $AA_2$ to use in a reaction mixture; Equations (3) and (4) are solved for $[AA_1]$ and $[AA_2]$ to give Equation (5):

$$\frac{[AA_2]}{[AA_1]} = \frac{k_{AA-1}[\text{peptide}-AA_2]}{k_{AA-2}[\text{peptide}-AA_1]} \quad (5)$$

Since equimolar concentrations of Peptide–$AA_1$ and Peptide–$AA_2$ are desired equation (5) simplifies to Equation (6):

$$\frac{[AA_2]}{[AA_1]} = \frac{k_{AA-1}}{k_{AA-2}} \quad (6)$$

The ratio in Equation (6) was determined using the following modification of the *Biopolymers* article procedure. Thus, instead of cleaving and hydrolysing the peptide with 6N hydrochloric acid, equimolar amounts of Peptide–$AA_1$ and Peptide–$AA_2$, each bound separately to the same type of solid support used in the reactions of $AA_1$ and $AA_2$, were mixed with the reaction mixtures. The peptides were then cleaved and analyzed by HPLC (5–65%B in 30 minutes, Vydac 218TP54, A:0.05% TFA/$H_2O$, B:0.05% TFA/ACN, 214nm).

The relative ratios for the reactive subunits determined by the above methodology are set forth below in Tables 2 and 3:

TABLE 2

| No. | N-α-Fmoc AA | Ratio |
|---|---|---|
| 1 | Fmoc-Ala | 0.83 |
| 2 | Fmoc-Phe | 0.61 |
| 3 | Fmoc-Gly | 1.00 |
| 4 | Fmoc-Ile | 1.20 |
| 5 | Fmoc-Lys (Boc) | 1.02 |
| 6 | Fmoc-Leu | 0.93 |
| 7 | Fmoc-Met (O) | 0.57 |
| 8 | Fmoc-Asn (Trt) | 0.98 |
| 9 | Fmoc-Gln (Trt) | 1.01 |
| 10 | Fmoc-Arg (Pmc) | 1.20 |
| 11 | Fmoc-Ser (tBu) | 0.64 |
| 12 | Fmoc-Thr (tBu) | 0.87 |
| 13 | Fmoc-Val | 1.14 |
| 14 | Fmoc-Trp (Boc) | 0.69 |
| 15 | Fmoc-Trp | 0.69 |
| 16 | Fmoc-Tyr (Brz) | 0.67 |
| 17 | Fmoc-Tyr (tBu) | 0.67 |
| 18 | Fmoc-ala | 0.83 |
| 19 | Fmoc-phe | 0.61 |
| 20 | Fmoc-ile | 1.20 |
| 21 | Fmoc-lys (Boc) | 1.02 |
| 22 | Fmoc-leu | 0.93 |
| 23 | Fmoc-asn (Trt) | 0.98 |
| 24 | Fmoc-gln (Trt) | 1.01 |
| 25 | Fmoa-ser (tBu) | 0.64 |
| 26 | Fmoc-thr (tBu) | 0.87 |
| 27 | Fmoc-val | 1.14 |
| 28 | Fmoc-trp (Boc) | 0.69 |
| 29 | Fmoc-trp | 0.69 |
| 30 | Fmoc-tyr (tBu) | 0.67 |
| 31 | Fmoc-arg (Pmc) | 1.20 |
| 32 | Fmoc-Nle | 0.94 |
| 33 | Fmoc-nle | 0.94 |
| 34 | Fmoc-Nve | 0.96 |
| 35 | Fmoc-nve | 0.96 |
| 36 | Fmoc-Nal | 0.67 |

TABLE 2-continued

| No. | N-α-Fmoc AA | Ratio |
|-----|-------------|-------|
| 37 | Fmoc-nal | 0.67 |
| 38 | Fmoc-Phg | 0.48 |
| 39 | Fmoc-Glu (tBu) | 0.73 |
| 40 | Fmoc-glu (tBu) | 0.73 |
| 41 | Fmoc-Cha | 0.94 |
| 42 | Fmoc-cha | 0.94 |
| 43 | Fmoc-pCl-Phe | 1.00 |
| 44 | Fmoc-pCl-phe | 1.00 |
| 45 | Fmoc-pya | 1.00 |

TABLE 3

| No. | N-α-Boc AA | Ratio |
|-----|------------|-------|
| 1 | Ala | 0.95 |
| 2 | Phe | 0.81 |
| 3 | Gly | 1.00 |
| 4 | Ile | 1.16 |
| 5 | Lys (Clz) | 1.05 |
| 6 | Leu | 1.08 |
| 7 | Met (O) | 0.89 |
| 8 | Asn | 1.20 |
| 9 | Gln | 1.20 |
| 10 | Arg (Tos) | 1.42 |
| 11 | Ser (Bzl) | 1.30 |
| 12 | Thr (Bzl) | 1.60 |
| 13 | Val | 1.14 |
| 14 | Trp (CHO) | 0.89 |
| 15 | Tyr (Brz) | 1.26 |
| 16 | Tyr (2,6-diClBzl) | 1.30 |
| 17 | ala* | 0.95 |
| 18 | phe | 0.81 |
| 19 | ile | 1.16 |
| 20 | lys (Clz) | 1.05 |
| 21 | leu | 1.08 |
| 22 | asn | 1.20 |
| 23 | gln | 1.20 |
| 24 | arg (Tos) | 1.42 |
| 25 | ser (Bzl) | 1.30 |
| 26 | thr (Bzl) | 1.60 |
| 27 | val | 1.14 |
| 28 | trp (CHO) | 0.89 |
| 29 | tyr (Brz) | 1.26 |
| 30 | tyr (2,6-diClBzl) | 1.30 |
| 31 | α-Aba | 0.94 |
| 32 | γ-Aba | 1.58 |
| 33 | α-Aib | 1.66 |
| 34 | Nve | 1.15 |
| 35 | nve | 1.15 |
| 36 | Nle | 1.15 |
| 37 | nle | 1.15 |
| 38 | ε-Aca | 3.68 |
| 39 | 7-Aca | 3.20 |
| 40 | ε-Lys (Clz) | 1.05 |
| 41 | Orn (Cbz) | 1.06 |
| 42 | δ-Orn (Cbz) | 1.04 |
| 43 | Phg | 0.66 |
| 44 | phg | 0.66 |
| 45 | Nal | 0.55 |
| 46 | nal | 0.55 |
| 47 | β-Ala | 2.00 |
| 48 | Cha | 1.50 |
| 49 | cha | 1.50 |
| 50 | pCl-Phe | 1.00 |
| 51 | pCl-phe | 1.00 |
| 52 | pNO₂-Phe | 1.00 |
| 53 | pNO₂-phe | 1.00 |
| 54 | pI-Phe | 1.00 |
| 55 | Tha | 1.00 |
| 56 | tha | 1.00 |
| 57 | Pya | 1.00 |
| 58 | pya | 1.00 |
| 59 | pF-Phe | 1.00 |
| 60 | pF-phe | 1.00 |

TABLE 3-continued

| No. | N-α-Boc AA | Ratio |
|-----|------------|-------|
| 61 | Met (O₂) | 0.90 |
| 62 | Trp | 0.89 |
| 63 | isoAsn | 1.50 |
| 64 | isoGln | 1.70 |
| 65 | Chg | 2.00 |
| 66 | tBu-Gly | 2.00 |
| 67 | Lys (Ac) | 0.90 |
| 68 | Cys (MeOBzl) | 1.00 |
| 69 | Asp (Bzl) | 0.90 |
| 70 | Glu (Bzl) | 0.95 |
| 71 | His (Dnp) | 0.85 |
| 72 | cys (MeOBzl) | 1.00 |
| 73 | asp (Bzl) | 0.90 |
| 74 | glu (Bzl) | 0.95 |
| 75 | his (Dnp) | 0.85 |
| 76 | p-benzoyl-phe | 1.80 |
| 77 | pNH₂-Phe (Fmoc) | 1.25 |
| 78 | Asp (Fm) | 1.00 |
| 79 | tyr (Et) | 1.20 |
| 80 | eLys (Fmoc) | 1.10 |
| 81 | Orn (Fmoc) | 1.00 |
| 82 | Lys (Fmoc) | 1.10 |
| 83 | pNH₂-phe (Fmoc) | 1.25 |
| 84 | Tyr (Et) | 1.20 |
| 85 | lys (Fmoc) | 1.10 |
| 86 | Glu (Fm) | 1.20 |
| 87 | pI-phe | 1.00 |
| 88 | trp | 0.89 |
| 89 | His (Tos) | 0.85 |
| 90 | his (Tos) | 0.85 |
| 91 | β-Asp (Bzl) | 1.5 |
| 92 | γ-Glu (Bzl) | 2.0 |

*lower case denotes D-Amino acids

This example provides the synthesis of a non-alkylated hydantoin combinatorial library of the present invention; (1) X=O, $R^2$=H, $R^4$=H, $R^5$=H. The $R^1$ and $R^3$ groups varied as described above and below. Eighty-two first Boc protected amino acids were used, generating at least eighty-two $R^1$ groups, depending on the modifications to the side chains. The amino acids used to generate $R^1$ are again listed below in Table 4. Seventy-two second Boc protected amino acids were used to generate the various $R^3$ groups, which amino acids are also again summarized in Table 4 below. Therefore, Table 4 provides a summary of all the amino acids ($R^1$ and $R^3$) used in the preparation of the library.

TABLE 4

SUMMARY OF R GROUPS IN NON-ALKYLATED HYDANTOIN LIBRARY

| | $R^1$ | $R^3$ | | $R^1$ | $R^3$ |
|---|---|---|---|---|---|
| 1 | Ala | Ala | 45 | Nal | Cys (MeoBzl) |
| 2 | Phe | Phe | 46 | nal | Asp (Bzl) |
| 3 | Gly | Gly | 47 | β-Ala | Glu (Bzl) |
| 4 | Ile | Ile | 48 | Cha | His (Dnp) |
| 5 | Lys (Clz) | Leu | 49 | cha | cys (MeCBzl) |
| 6 | Leu | Lys (Clz) | 50 | pNO₂-Phe | asp (Bzl) |
| 7 | Met (O) | Met (O) | 51 | pNO₂-phe | glu (Bzl) |
| 8 | Asn | Arg (Tos) | 52 | Chg | his (Dnp) |
| 9 | Gln | Ser (Bzl) | 53 | pI-Phe | Tha |
| 10 | Arg (Tos) | Thr (Bzl) | 54 | pCl-phe | tha |
| 11 | Ser (Bzl) | Val | 55 | tBu-Gly | pya |
| 12 | Thr (Bzl) | Trp (CHO) | 56 | Lys (Ac) | pF-phe |
| 13 | Val | Tyr (Brz) | 57 | pF-Phe | pI-phe |
| 14 | Trp (CHO) | ala* | 58 | Cys (MeoBzl) | p-benzoyl-phe |
| 15 | Tyr (Brz) | phe | 59 | Asp (Bzl) | Asp (Fm) |
| 16 | ala | ile | 60 | Glu (Bzl) | tyr (Et) |
| 17 | phe | lys (Clz) | 61 | His (Dnp) | Tyr (Et) |

TABLE 4-continued

SUMMARY OF R GROUPS IN NON-ALKYLATED HYDANTOIN LIBRARY

| | $R^1$ | $R^3$ | | $R^1$ | $R^3$ |
|---|---|---|---|---|---|
| 18 | ile | leu | 62 | cys (MeoBzl) | Orn (Fmoc) |
| 19 | lys (Clz) | arg (Tos) | 63 | asp (Bzl) | Lys (Fmoc) |
| 20 | leu | ser (Bzl) | 64 | glu (Bzl) | p-NH$_2$-phe (Fmoc) |
| 21 | asn | thr (Bzl) | 65 | his (Dnp) | Pya |
| 22 | gln | val | 66 | Tha | lys (Fmoc) |
| 23 | arg (Tos) | tyr (Brz) | 67 | tha | Glu (Fm) |
| 24 | ser (Bzl) | α-Aba | 68 | pya | pNH$_2$-Phe (Fmoc) |
| 25 | thr (Bzl) | α-Aib | 69 | pF-phe | pCl-Phe |
| 26 | val | Nve | 70 | pI-phe | trp |
| 27 | pCl-Phe | nve | 71 | p-benzoyl-phe | His (Tos) |
| 28 | tyr (Brz) | Nle | 72 | pNH$_2$-Phe (Fmoc) | his (tos) |
| 29 | Tyr (2,6-diClBzl) | nle | 73 | Asp (Fm) | |
| 30 | tyr(2,6-diClBzl) | Orn (Cbz) | 74 | tyr (Et) | |
| 31 | α-Aba | Phg | 75 | ε-Lys (Fmoc) | |
| 32 | γ-Aba | phg | 76 | Orn (Fmoc) | |
| 33 | α-Aib | Nal | 77 | Lys (Fmoc) | |
| 34 | Nve | nal | 78 | pNH$_2$-phe (Fmoc) | |
| 35 | nve | Cha | 79 | Pya | |
| 36 | Nle | cha | 80 | Tyr (Et) | |
| 37 | nle | pNO$_2$-Phe | 81 | lys (Fmoc) | |
| 38 | ε-Aca | pNO$_2$-phe | 82 | Glu (Fm) | |
| 39 | 7-Aha | Chg | | | |
| 40 | ε-Lys (Clz) | pI-Phe | | | |
| 41 | Orn (Cbz) | pCl-phe | | | |
| 42 | δ-Orn (Cbz) | tBu-Gly | | | |
| 43 | Phg | Lys (Ac) | | | |
| 44 | phg | pF-Phe | | | |

*lower case lettering indicates D-amino acids

The pools of this library were prepared in the iterative scan format. A typical procedure for the combinatorial synthesis of the subject non-alkylated hydantoin library was as follows. One hundred milligrams of p-methylbenzhydrylamine (MBHA) resin (0.81 meq/g, 100–200 mesh) was contained within a sealed polypropylene mesh packet. Reactions were carried out in a 10 ml polyethylene bottle. Following neutralization with 5% diisopropylethylamine (DIEA) in dichloromethane (DCM), the resin was washed with DCM. The first Boc-protected amino acid (protected amino acid in FIG. 1)(6×) was coupled using the conventional reagents hydroxybenzotriazole (HOBt) (6×) and diisopropylcarbodiimide (DICI)(6×)(final concentration =0.1M in DMF) using predetermined ratios discussed above in the Introduction Section. The Boc protecting group was then removed with 55% TFA in CH$_2$Cl$_2$. Following neutralization with 5% diisopropylethylamine (DIEA) in dichloromethane (DCM), the resin was washed with DCM. The second Boc-protected amino acid (protected amino acid in FIG. 1)(6×) was coupled using the conventional reagents hydroxybenzotriazole (HOBt)(6×) and diisopropylcarbodiimide (DICI) (6×) (final concentration=0.1M in DMF). The Boc protecting group was then removed with 55% TFA in CH$_2$Cl$_2$. Following neutralization with 5% diisopropylethylamine (DIEA) in dichloromethane (DCM), the resin was washed with DCM.

Hydantoins were formed following treatment of the dipeptide for fifteen minutes with 24-fold excess of triphosgene (0.1M in anhydrous dichloromethane with 5-fold excess of DIEA over dipeptide). The solution was then removed, and the resin washed with dry dichloromethane. Dry dichloromethane was added and the resin shaken for 12 hours to allow the cyclization to go to completion. The amino acid side chains were removed using the "low HF" procedure of Tam, et al. *Int. J. Pep. Prot. Res.*, 21:57 (1983), which is incorporated herein by reference. Following cleavage from the resin with anhydrous HF by the procedures of Houghten et al. *Int. J. Pep. Prot. Res.*, 27:673 (1986), which is incorporated herein by reference, in the presence of anisole, the desired products were extracted and lyophilized. The desired products were obtained in good yields and high purity following lyophilization.

EXAMPLE II

Following the procedures of Example I, seventy-two pools of libraries containing non-alkylated hydantoins were prepared in the iterative format having $R^1$ as a mixture and $R_3$ constant as listed above 1 through 72 for the $R^3$ variable in Table 4. Each of the seventy-two pools were screened in an anti-microbial assay, which assay procedure is described in detail above. The results of this screen are provided in Table 5 below.

The results of the assay evidence that many of the hydantoins compounds contained within the library are biologically active as an anti-microbial.

TABLE 5

Assay Of The Non-alkylated Library (Iterative Format)

| Pool No. | Anti-Microbial Assay (IC$_{50}$, μg/ml) | Pool No. | Anti-Microbial Assay (IC$_{50}$, μg/ml) |
|---|---|---|---|
| 1 | >62.5 | 37 | >62.5 |
| 2 | >62.5 | 38 | >62.5 |
| 3 | >62.5 | 39 | >62.5 |
| 4 | >62.5 | 40 | 54.0 |
| 5 | >62.5 | 41 | >62.5 |
| 6 | >62.5 | 42 | >62.5 |
| 7 | >62.5 | 43 | >62.5 |
| 8 | >62.5 | 44 | >62.5 |
| 9 | >62.5 | 45 | >62.5 |
| 10 | >62.5 | 46 | >62.5 |
| 11 | >62.5 | 47 | >62.5 |
| 12 | >62.5 | 48 | >62.5 |
| 13 | >62.5 | 49 | >62.5 |
| 14 | >62.5 | 50 | >62.5 |
| 15 | >62.5 | 51 | >62.5 |
| 16 | >62.5 | 52 | >62.5 |
| 17 | >62.5 | 53 | >62.5 |
| 18 | >62.5 | 54 | >62.5 |
| 19 | >62.5 | 55 | >62.5 |
| 20 | >62.5 | 56 | >62.5 |
| 21 | >62.5 | 57 | >62.5 |
| 22 | >62.5 | 58 | >62.5 |
| 23 | >62.5 | 59 | >62.5 |
| 24 | >62.5 | 60 | >62.5 |
| 25 | >62.5 | 61 | >62.5 |
| 26 | >62.5 | 62 | 41.0 |
| 27 | >62.5 | 63 | 47.0 |
| 28 | >62.5 | 64 | >62.5 |
| 29 | >62.5 | 65 | >62.5 |
| 30 | >62.5 | 66 | >62.5 |
| 31 | >62.5 | 67 | >62.5 |
| 32 | >62.5 | 68 | >62.5 |
| 33 | 53.0 | 69 | >62.5 |
| 34 | >62.5 | 70 | >62.5 |
| 35 | >62.5 | 71 | >62.5 |
| 36 | >62.5 | 72 | >62.5 |

This example provides the synthesis of a non-alkylated thiohydantoin combinatorial library of the present invention; (1) X=S, $R^2$=$R^4$=$R^5$=H. The $R^1$, and $R^3$ groups were identical to those used in Example I and provided in Table 4 above with the following exceptions. For $R^1$, Tyr(2,6-diClBzl), tyr(2,6-diClBzl), Cys(MeoBzl), cys(MeoBzl) and pI-phe were not used as in Example I and ten alternative amino acids were used as provided in Table 6 below. Therefore, a total of eighty-seven first Boc protected amino acids were used using predetermined ratios as set forth above in the Introduction, generating at least eighty-seven $R^1$ groups, depending on the modifications to the side chains.

Seventy-four second Boc protected amino acids were used to generate the various $R^3$ groups using the above predetermined ratios. Sixty-seven were identical to those used in Example I and provided in Table 4. For $R^3$, Cys (MeoBzl), cys(MeoBzl) and pI-phe, his(Tos) and α-Aib were not used as in Example I and instead the seven alternative amino acids listed in Table 6 below were used, for a total of seventy-four. Therefore, Table 6 provides a summary of all the additional amino acids ($R^1$ and $R^3$) used in the preparation of the non-alkylated thiohydantoin library compared to Example I, Table 4.

TABLE 6

SUMMARY OF ADDITIONAL R GROUPS IN NON-ALKYLATED THIOHYDANTOIN LIBRARY

| | $R^1$ | $R^3$ | | $R^1$ | $R^3$ |
|---|---|---|---|---|---|
| 1 | Met (O₂) | Met (O₂) | 6 | trp* | asn |
| 2 | Trp | Trp | 7 | His (Tos) | gln |
| 3 | trp (CHO) | trp (CHO) | 8 | β-Asp (Bzl) | |
| 4 | isoAsn | Asn | 9 | γ-Glu (Bzl) | |
| 5 | isoGln | Gln | 10 | β-Asp (Fm) | |

*lower case lettering indicates D-amino acids

The pools of this library were prepared in the positional scan format. A typical procedure for the combinatorial synthesis of the subject non-alkylated thiohydantoin library was as follows. One hundred mg of p-methylbenzhydrylamine (MBHA) resin (0.81 meq/g, 100–200 mesh) was contained within a sealed polypropylene mesh packet. Reactions were carried out in a 10 ml polyethylene bottle. Following neutralization with 5% diisopropylethylamine (DIEA) in dichloromethane (DCM), the resin was washed with DCM. The first Boc-protected amino acid (protected amino acid in FIG. 1) was coupled using the conventional reagents hydroxybenzotriazole (HOBt) and diisopropylcarbodiimide (DICI) under the conditions described in Example I. The Boc protecting group was then removed with 55% TFA in CH₂Cl₂. Following neutralization with 5% diisopropylethylamine (DIEA) in dichloromethane (DCM), the resin was washed with DCM. The second Boc-protected amino acid (protected amino acid in FIG. 1) was coupled using the conventional reagents hydroxybenzotriazole (HOBt) and diisopropylcarbodiimide (DICI) under the conditions described in Example I. The Boc protecting group was then removed with 55% TFA in CH₂Cl₂. Following neutralization with 5% diisopropylethylamine (DIEA) in dichloromethane (DCM), the resin was washed with DCM.

Thiohydantoins were formed following treatment of the dipeptide for fifteen minutes with 24-fold excess of thiocarbonyldiimidazole (0.1M in dichloromethane anhydrous). The solution was then removed, the resin washed with dry dichloromethane. Dry dichloromethane was added and the resin shaken for 12 hours to allow the cyclization to go to completion. Following cleavage from the resin with anhydrous HF by the procedures of Houghten et al. *Int. J. Pep.* *Prot. Res.*, 27:673 (1986), which is incorporated herein by reference, in the presence of anisole, the desired products were extracted and lyophilized. The desired products were obtained in good yields and high purity following lyophilization.

EXAMPLE IV

Figure 2A:
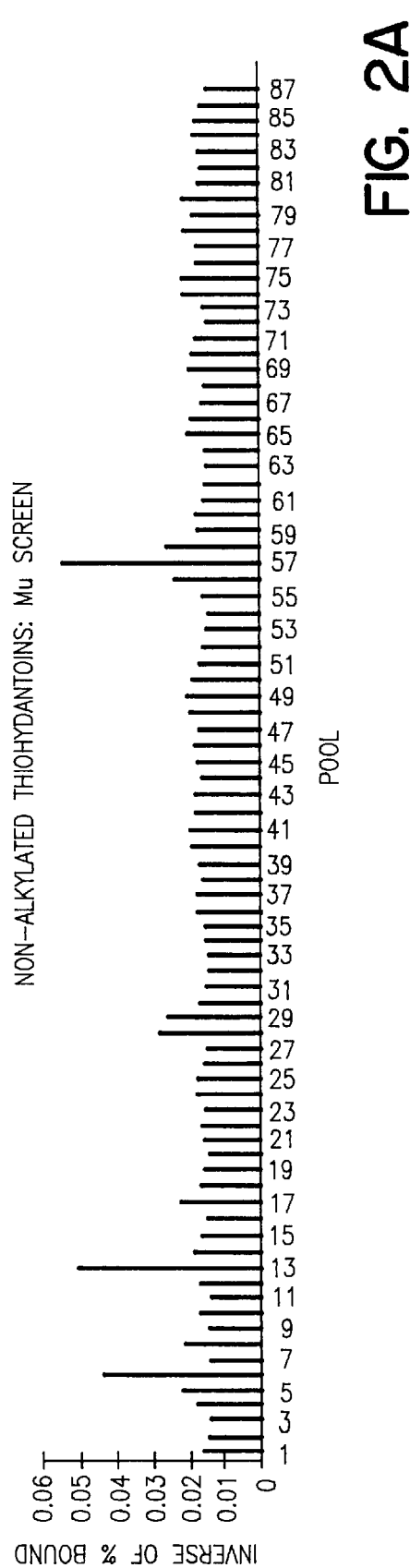
FIG. 2 graphically depicts the µ-opioid receptor screening data for the non-alkylated N-benzyl amninocyclic thiohydantoin library of the subject invention as provided in Example IV.
Figure 2B:
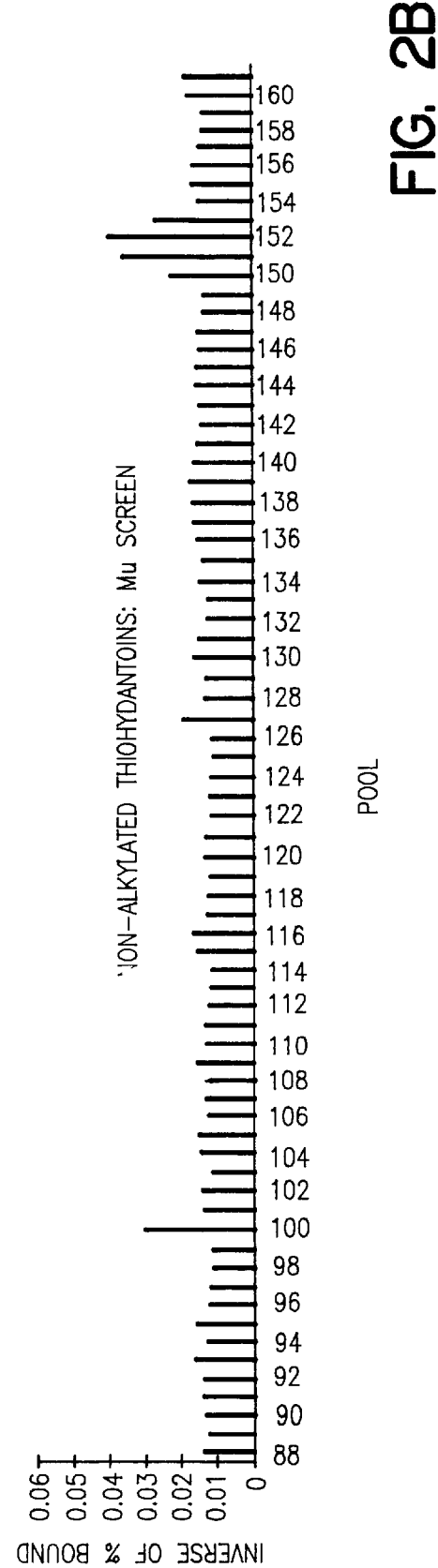

Following the procedures of Example III, the following pools of libraries containing non-alkylated thiohydantoins were prepared in the positional scan format. Therefore, X=S and $R^2$, $R^4$, $R^5$=hydrogen and the remaining R groups and their respective pool reference numbers are identified in Table 7 below. Each of the one hundred sixty-one pools were screened in (1) an anti-microbial assay, and (2) a μ-opioid receptor assay, each of which are described in detail above. The results of those screens are provided in Table 7 below and depicted graphically in FIG. 2.

The results of these assays evidence that many of the thiohydantoins contained within the library are biologically active, either as an anti-microbial or inhibitor of a specific opioid receptor.

TABLE 7

Assays Of The Thiohydantoin Library (Positional Scanning Format)

| Pool No. | $R^1$ | $R^3$ | Anti-Microbial Assay (IC₅₀, μg/ml) | μ-Opioid Receptor Assay (% Bound) |
|---|---|---|---|---|
| 1 | Ala | X | >250 | 61 |
| 2 | Asp (Bzl) | X | >250 | 78 |
| 3 | Glu (Bzl) | X | >250 | 75 |
| 4 | Phe | X | 96.3 | 56 |
| 5 | Gly | X | >250 | 47 |
| 6 | His (DNP) | X | 60.4 | 23 |
| 7 | Ile | X | 101.1 | 71 |
| 8 | Lys (Clz) | X | >250 | 50 |
| 9 | Leu | X | 123.7 | 70 |
| 10 | Met (O) | X | >250 | 63 |
| 11 | Asn | X | >250 | 76 |
| 12 | Gln | X | >250 | 58 |
| 13 | Arg (Tos) | X | 101.4 | 20 |
| 14 | Ser (Bzl) | X | >250 | 56 |
| 15 | Thr (Bzl) | X | >250 | 66 |
| 16 | Val | X | >250 | 69 |
| 17 | Trp (CHO) | X | >250 | 47 |
| 18 | Tyr (Brz) | X | >250 | 64 |
| 19 | ala* | X | >250 | 67 |
| 20 | asp (Bzl) | X | >250 | 76 |
| 21 | glu (Bzl) | X | >250 | 69 |
| 22 | phe | X | 112.3 | 66 |
| 23 | his (DNP) | X | 59.3 | 67 |
| 24 | ile | X | >250 | 62 |
| 25 | lys (Clz) | X | >250 | 60 |
| 26 | leu | X | 118.3 | 72 |
| 27 | asn | X | >250 | 67 |
| 28 | gln | X | >250 | 38 |
| 29 | arg (Tos) | X | 115.8 | 40 |
| 30 | ser (Bzl) | X | >250 | 64 |
| 31 | thr (Bzl) | X | >250 | 74 |
| 32 | val | X | >250 | 73 |
| 33 | trp (CHO) | X | >250 | 74 |
| 34 | tyr (Brz) | X | >250 | 75 |
| 35 | α-Aba | X | >250 | 70 |
| 36 | Nve | X | 105.5 | 63 |
| 37 | nve | X | 99.5 | 65 |
| 38 | Nle | X | 123.6 | 64 |
| 39 | nle | X | 53.1 | 61 |
| 40 | Orn (CBZ) | X | >250 | 55 |
| 41 | δ-Orn (CBZ) | X | 126.4 | 54 |
| 42 | Phg | X | 128.2 | 59 |

TABLE 7-continued

Assays Of The Thiohydantoin Library (Positional Scanning Format)

| Pool No. | R¹ | R³ | Anti-Microbial Assay (IC$_{50}$, μg/ml) | μ-Opioid Receptor Assay (% Bound) |
|---|---|---|---|---|
| 43 | phg | X | 124.9 | 59 |
| 44 | Nal | X | 117.2 | 66 |
| 45 | nal | X | 105.2 | 60 |
| 46 | Cha | X | 85.9 | 57 |
| 47 | cha | X | 99.1 | 60 |
| 48 | Lys (Fmoc) | X | 95.7 | 56 |
| 49 | lys (Fmoc) | X | 85.8 | 53 |
| 50 | Met (O$_2$) | X | 152.0 | 54 |
| 51 | pNO$_2$-Phe | X | 89.5 | 63 |
| 52 | pNO$_2$-phe | X | 118.9 | 66 |
| 53 | pCl-Phe | X | 49.1 | 69 |
| 54 | pCl-phe | X | 44.6 | 66 |
| 55 | pF-Phe | X | 132.7 | 63 |
| 56 | pF-phe | X | 51.0 | 41 |
| 57 | Lys (Ac) | X | >250 | 18 |
| 58 | Pya | X | >250 | 39 |
| 59 | pya | X | >250 | 59 |
| 60 | Tha | X | >250 | 58 |
| 61 | tha | X | 45.8 | 64 |
| 62 | tBu-Gly | X | >250 | 67 |
| 63 | Tyr (Et) | X | >250 | 70 |
| 64 | tyr (Et) | X | >250 | 66 |
| 65 | pNH$_2$-phe (Fmoc) | X | 29.6 | 53 |
| 66 | trp | X | >250 | 53 |
| 67 | pNH$_2$-Phe (Fmoc) | X | 38.6 | 64 |
| 68 | Asp (Fm) | X | >250 | 66 |
| 69 | p-benzoyl-phe | X | >250 | 53 |
| 70 | pI-Phe | X | 75.4 | 52 |
| 71 | Chg | X | >250 | 59 |
| 72 | Orn (Fmac) | X | >250 | 71 |
| 73 | Glu (Fm) | X | 134.9 | 67 |
| 74 | His (Tos) | X | >250 | 50 |
| 75 | Trp | X | >250 | 48 |
| 76 | γ-Aba | X | >250 | 59 |
| 77 | α-Aib | X | >250 | 58 |
| 78 | ε-Aca | X | >250 | 49 |
| 79 | 7-Aha | X | 120.4 | 55 |
| 80 | ε-Lys (Clz) | X | 105.5 | 50 |
| 81 | β-Ala | X | >250 | 62 |
| 82 | β-Asp (Bzl) | X | >250 | 85 |
| 83 | γ-Glu (Bzl) | X | >250 | 64 |
| 84 | ε-Lys (Clz) | X | 131.8 | 58 |
| 85 | isoAsn | X | >250 | 72 |
| 86 | isoGln | X | >250 | 70 |
| 87 | β-Asp (Fm) | X | 115.9 | 69 |
| 88 | X | Ala | >250 | 72 |
| 89 | X | Asp (Bzl) | >250 | 80 |
| 90 | X | Glu (Bzl) | >250 | 78 |
| 91 | X | Phe | 149.1 | 67 |
| 92 | X | Gly | >250 | 74 |
| 93 | X | His (DNP) | 56.6 | 62 |
| 94 | X | Ile | >250 | 78 |
| 95 | X | Lys (Clz) | >250 | 65 |
| 96 | X | Leu | >250 | 86 |
| 97 | X | Met (O) | >250 | 83 |
| 98 | X | Asn | >250 | 86 |
| 99 | X | Gln | >250 | 90 |
| 100 | X | Arg (Tos) | 61.1 | 33 |
| 101 | X | Ser (Bzl) | 31.5 | 78 |
| 102 | X | Thr (Bzl) | 134.9 | 74 |
| 103 | X | Val | >250 | 89 |
| 104 | X | Trp (CHO) | 116.6 | 69 |
| 105 | X | Tyr (Brz) | >250 | 67 |
| 106 | X | ala | >250 | 84 |
| 107 | X | asp (Bzl) | >250 | 86 |
| 108 | X | glu (Bzl) | 129.8 | 73 |
| 109 | X | phe | >250 | 65 |
| 110 | X | his (Dnp) | 108.6 | 77 |
| 111 | X | ile | >250 | 79 |
| 112 | X | lys (Clz) | >250 | 80 |
| 113 | X | leu | >250 | 87 |
| 114 | X | asn | >250 | 88 |
| 115 | X | gln | >250 | 63 |
| 116 | X | arg (Tos) | 125.0 | 59 |
| 117 | X | ser (Bzl) | 36.7 | 80 |
| 118 | X | thr (Bzl) | 107.7 | 85 |
| 119 | X | val | >250 | 82 |
| 120 | X | trp (CHO) | 110.4 | 72 |
| 121 | X | tyr (Brz) | >250 | 78 |
| 122 | X | α-Aba | >250 | 84 |
| 123 | X | Nve | >250 | 84 |
| 124 | X | nve | 122.8 | 93 |
| 125 | X | Nle | 124.4 | 93 |
| 126 | X | nle | 105.2 | 83 |
| 127 | X | Orn (CBZ) | >250 | 52 |
| 128 | X | Phg | >250 | 80 |
| 129 | X | phg | >250 | 75 |
| 130 | X | Nal | 99.4 | 63 |
| 131 | X | nal | 112.7 | 72 |
| 132 | X | Cha | >250 | 85 |
| 133 | X | cha | >250 | 83 |
| 134 | X | Lys (Fmoc) | >250 | 74 |
| 135 | X | lys (Fmoc) | 107.9 | 70 |
| 136 | X | Met (O$_2$) | >250 | 68 |
| 137 | X | pNO$_2$-Phe | 159.5 | 65 |
| 138 | X | pNO$_2$-phe | >250 | 64 |
| 139 | X | pCl-Phe | 90.1 | 62 |
| 140 | X | pCl-phe | 105.8 | 64 |
| 141 | X | pF-Phe | 136.5 | 71 |
| 142 | X | pF-phe | >250 | 78 |
| 143 | X | Lys (Ac) | >250 | 69 |
| 144 | X | Pya | 181.4 | 61 |
| 145 | X | pya | >250 | 69 |
| 146 | X | Tha | >250 | 71 |
| 147 | X | tha | 141.9 | 71 |
| 148 | X | tBu-Gly | 158.1 | 77 |
| 149 | X | Tyr (Et) | >250 | 79 |
| 150 | X | tyr (Et) | 103.7 | 45 |
| 151 | X | PNH$_2$-phe (Fmoc) | 62.5 | 28 |
| 152 | X | trp | 45.0 | 25 |
| 153 | X | pNH$_2$-Phe (Fmoc) | 65.8 | 39 |
| 154 | X | Asp (Fm) | >250 | 70 |
| 155 | X | p-benzoyl-phe | >250 | 65 |
| 156 | X | pI-Phe | 98.3 | 63 |
| 157 | X | Chg | 75.5 | 70 |
| 158 | X | Orn (Fmoc) | 94.9 | 82 |
| 159 | X | Glu (Fm) | 106.1 | 76 |
| 160 | X | His (Tos) | 168.9 | 59 |
| 161 | X | Trp | 72.1 | 55 |

*lower case lettering indicates D-amino acids

EXAMPLE V

This example provides the synthesis of an alkylated hydantoin combinatorial library of the present invention; (1) X=O, R$^5$=H. The R$^1$, R$^2$, R$^3$ and R$^4$ groups varied as follows. Fifty-nine first Boc protected amino acids were used, generating at least fifty R$^1$ groups, depending on the modifications to the side chains. The amino acids used to generate $R^1$ are again listed below in Table 8. Four alkyl halides were used to generate the $R^2$ groups in the initial alkylation which are summarized in Table 8 below. Forty-five second Fmoc protected amino acids were used to generate the various $R^3$ groups, which amino acids are also summarized in the Table below. Finally, three $R^4$ groups were generated by performing a second N-alkylation with two alkyl halides while a third $R^4$ group (hydrogen, H) was the result of not alkylating. Therefore, Table 11 provides a summary of all the amino acids ($R^1$ and $R^3$) and alkyl groups ($R^2$ and $R^4$) used in the preparation of the libraries.

TABLE 8

SUMMARY OF R GROUPS IN ALKYLATED HYDANTOIN LIBRARY

| | $R^1$ | $R^2$ | $R^3$ | $R^4$ |
|---|---|---|---|---|
| 1 | Ala | methyl | Ala | hydrogen |
| 2 | Phe | ethyl | Phe | methyl |
| 3 | Gly | allyl | Gly | benzyl |
| 4 | Ile | benzyl | Ile | |
| 5 | Lys (Clz) | | Lys (Boc) | |
| 6 | Leu | | Leu | |
| 7 | Met (O) | | Met (O) | |
| 8 | Asn | | Asn (Trt) | |
| 9 | Gln | | Gln (Trt) | |
| 10 | Arg (Tos) | | Arg (Pmc) | |
| 11 | Ser (Bzl) | | Ser (tBu) | |
| 12 | Thr (Bzl) | | Thr (tBu) | |
| 13 | Val | | Val | |
| 14 | Trp (CHO) | | Trp (Boc) | |
| 15 | Tyr (Brz) | | Trp | |
| 16 | Tyr (2,6-diClBzl) | | Tyr (tBu) | |
| 17 | ala | | Tyr (Brz) | |
| 18 | phe | | ala | |
| 19 | ile | | phe | |
| 20 | lys (Clz) | | ile | |
| 21 | leu | | lys (Boc) | |
| 22 | asn | | leu | |
| 23 | gln | | asn (Trt) | |
| 24 | arg (Tos) | | gln (Trt) | |
| 25 | ser (Bzl) | | ser (tBu) | |
| 26 | thr (Bzl) | | thr (tBu) | |
| 27 | val | | val | |
| 28 | tyr (Brz) | | trp (Boc) | |
| 29 | tyr (2,6-diClBzl) | | trp | |
| 30 | α-Aba | | tyr (tBu) | |
| 31 | γ-Aba | | arg (Pmc) | |
| 32 | α-Aib | | Nle | |
| 33 | Nve | | nle | |
| 34 | nve | | Nve | |
| 35 | Nle | | nve | |
| 36 | nle | | Nal | |
| 37 | ε-Aca | | nal | |
| 38 | 7-Aha | | Phg | |
| 39 | ε-Lys (Clz) | | Glu (tBu) | |
| 40 | Orn (Cbz) | | glu (tBu) | |
| 41 | δ-Orn (Cbz) | | Cha | |
| 42 | Phg | | cha | |
| 43 | phg | | pCl-Phe | |
| 44 | Nal | | pCl-phe | |
| 45 | nal | | pya | |
| 46 | β-Ala | | | |
| 47 | Cha | | | |
| 48 | cha | | | |
| 49 | pCl-Phe | | | |
| 50 | pCl-phe | | | |
| 51 | pNO$_2$-Phe | | | |
| 52 | pNO$_2$-phe | | | |
| 53 | pI-Phe | | | |
| 54 | Tha | | | |
| 55 | tha | | | |
| 56 | Pya | | | |

TABLE 8-continued

SUMMARY OF R GROUPS IN ALKYLATED HYDANTOIN LIBRARY

| | $R^1$ | $R^2$ | $R^3$ | $R^4$ |
|---|---|---|---|---|
| 57 | pya | | | |
| 58 | pF-Phe | | | |
| 59 | pF-phe | | | |

*lower case lettering indicates D-amino acids

The pools of this library were prepared in the positional scan format. A typical procedure for the combinatorial synthesis of the subject alkylated hydantoin library was as follows. One hundred and eighty mg of p-methylbenzhydrylamine (MBRA) resin (0.81 meq/g, 100–200 mesh) was contained within a sealed polypropylene mesh packet. Reactions were carried out in a 10 ml polyethylene bottle. Following neutralization with 5% diisopropylethylamine (DIEA) in dichloromethane (DCM), the resin was washed with DCM. The first Boc-protected amino acid (protected amino acid in FIG. 1) was coupled using the conventional reagents hydroxybenzotriazole (HOBt) and diisopropylcarbodiimide (DICI) using the predetermined ratios set forth in the Introduction and under the conditions described in Example I. The Boc protecting group was then removed with 55% TFA in $CH_2Cl_2$. Following neutralization with 5% diisopropylethylamine (DIEA) in dichloromethane (DCM) and was washing with DCM, the mesh packet was shaken overnight in a solution of trityl chloride in DCM/DMF (9:1) in the presence of DIEA. Completeness of the trityl coupling was verified using the bromophenol blue color test as described in Krchnak et al. *Coll. Czech. Chem. Commun.*, 53:2542 (1988), which is incorporated herein by reference.

N-alkylation was then performed by treatment of the resin packet with 1M lithium t-butoxide in THF. Excess base was removed by cannulation, followed by addition of the individual alkylating agent in DMSO. The solution was vigorously shaken for 2 h at room temperature. Upon removal of the trityl group with 2% TFA in DCM (2×10 min), the packet was washed, neutralized and the second Fmoc-protected amino acid (protected amino acid in FIG. 1) coupled using the above predetermined ratios set forth in the Introduction and under the conditions described in Example I.

Following removal of the Fmoc group, hydantoins were formed following treatment for fifteen minutes with triphosgene (0.1M in dichloromethane anhydrous with 0.04M DIEA). The solution was then removed, the resin washed with dry dichloromethane. Dry dichloromethane was added and the resin shaken for 12 hours to allow the cyclization to go to completion, followed by washing with dichloromethane.

N-alkylation was then performed by treatment of the resin packet with 1M sodium cyclopentadienylide in THF. Excess base was removed by cannulation, followed by addition of the individual alkylating agent in DMSO. The solution was vigorously shaken for 2 h at room temperature.

Following cleavage from the resin with anhydrous HF by the procedures of Houghten et al. *Int. J. Pep. Prot, Res.*, 27:673 (1986), which is incorporated herein by reference, in the presence of anisole, the desired products were extracted and lyophilized. The desired products were obtained in good yields and high purity following lyophilization.

EXAMPLE VI

Figure 3D:
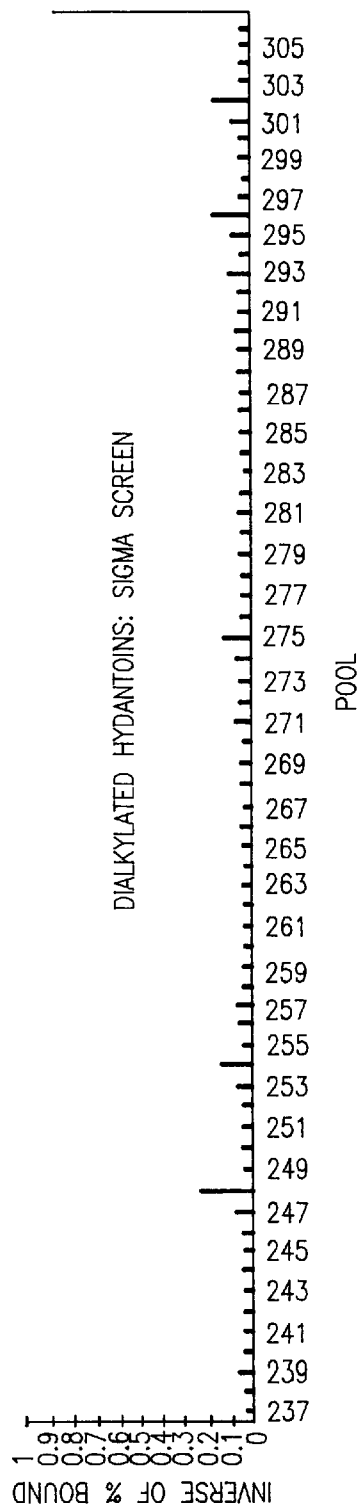
FIG. 3 shows graphically the a receptor screening data for the di-alkylated hydantoin library as detailed in Example VI.
Figure 3E:
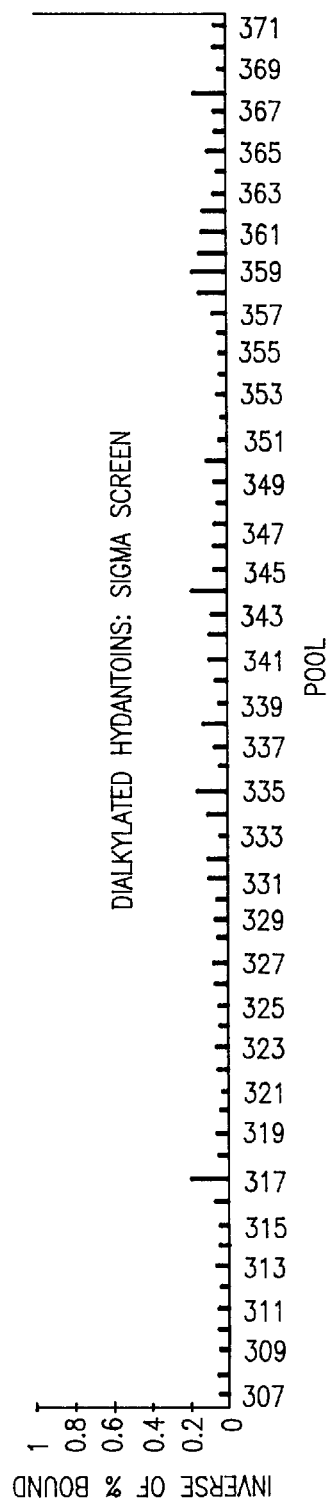

Following the procedures of Example V, the pools of libraries containing alkylated hydantoins were prepared in the positional scan format. Therefore, X=O and $R^5$ =hydrogen and the remaining R groups and their respective pool reference numbers ("No.") are identified in Table 9 below. Each of the three hundred and seventy one pools containing all the alkylated hydantoins were screened in (1) an anti-microbial assay ("AM" column in Table 9, reported as $IC_{50}$, μg/ml), (2) a σ receptor assay ("σ" column in Table 7, reported as % bound, 0.008 mg/ml) and (3) a k-opioid receptor assay ("K" column in Table 7, reported as % bound, 0.008 mg/ml), each of which are described in detail above. The results of the latter two assays are also provided graphically in FIGS. 3 and 4, respectively.

The results of these assays evidence that many of the alkylated hydantoins contained within the library are biologically active, either as an anti-microbial or inhibitor of a specific receptor. Moreover, the results of the screens provide evidence that there is selectivity of certain compounds for one receptor over another.

TABLE 9

Assays Of The Alkylated Hydantoin Library (Positional Scanning Format)

| No. | $R^1$ | $R^2$ | $R^3$ | $R^4$ | AM | σ | κ |
|---|---|---|---|---|---|---|---|
| 1 | Ala | methyl | X | X | >125 | 58 | 3 |
| 2 | Ala | ethyl | X | X | >125 | 53 | 9 |
| 3 | Ala | allyl | X | X | >125 | 51 | 16 |
| 4 | Ala | benzyl | X | X | >125 | 39 | 13 |
| 5 | Phe | methyl | X | X | >125 | 61 | 16 |
| 6 | Phe | ethyl | X | X | >125 | 58 | 20 |
| 7 | Phe | allyl | X | X | >125 | 53 | 24 |
| 8 | Phe | benzyl | X | X | >125 | 59 | 24 |
| 9 | Gly | methyl | X | X | >125 | 37 | 14 |
| 10 | Gly | ethyl | X | X | >125 | 41 | 15 |
| 11 | Gly | allyl | X | X | >125 | 37 | 20 |
| 12 | Gly | benzyl | X | X | >125 | 29 | 13 |
| 13 | Ile | methyl | X | X | >125 | 52 | 29 |
| 14 | Ile | ethyl | X | X | >125 | 66 | 36 |
| 15 | Ile | allyl | X | X | >125 | 55 | 53 |
| 16 | Ile | benzyl | X | X | >125 | 63 | 28 |
| 17 | Lys (Clz) | methyl | X | X | 68.9 | 18 | 11 |
| 18 | Lys (Clz) | ethyl | X | X | 65.4 | 8 | 16 |
| 19 | Lys (Clz) | allyl | X | X | 58.5 | 6 | 4 |
| 20 | Lys (Clz) | benzyl | X | X | 25.7 | 0 | 4 |
| 21 | Leu | methyl | X | X | >125 | 53 | 17 |
| 22 | Leu | ethyl | X | X | >125 | 52 | 30 |
| 23 | Leu | allyl | X | X | >125 | 57 | 35 |
| 24 | Leu | benzyl | X | X | >125 | 52 | 21 |
| 25 | Met (O) | methyl | X | X | >125 | 57 | 17 |
| 26 | Met (O) | ethyl | X | X | >125 | 53 | 28 |
| 27 | Met (O) | allyl | X | X | >125 | 33 | 15 |
| 28 | Met (O) | benzyl | X | X | 119.9 | 42 | 7 |
| 29 | Asn | methyl | X | X | >125 | 67 | 9 |
| 30 | Asn | ethyl | X | X | >125 | 63 | 19 |
| 31 | Asn | allyl | X | X | >125 | 21 | 26 |
| 32 | Asn | benzyl | X | X | >125 | 19 | 3 |
| 33 | Gln | methyl | X | X | >125 | 86 | 29 |
| 34 | Gln | ethyl | X | X | >125 | 65 | 18 |
| 35 | Gln | allyl | X | X | >125 | 15 | 20 |
| 36 | Gln | benzyl | X | X | >125 | 48 | 0 |
| 37 | Arg (Tos) | methyl | X | X | 17.1 | 55 | 0 |
| 38 | Arg (Tos) | ethyl | X | X | 14.5 | 46 | 0 |
| 39 | Arg (Tos) | allyl | X | X | 11.2 | 18 | 6 |
| 40 | Arg (Tos) | benzyl | X | X | 11.8 | 50 | 0 |
| 41 | Ser (Bzl) | methyl | X | X | >125 | 83 | 38 |
| 42 | Ser (Bzl) | ethyl | X | X | >125 | 63 | 24 |
| 43 | Ser (Bzl) | allyl | X | X | >125 | 50 | 44 |
| 44 | Ser (Bzl) | benzyl | X | X | >125 | 65 | 28 |
| 45 | Thr (Bzl) | methyl | X | X | >125 | 52 | 32 |
| 46 | Thr (Bzl) | ethyl | X | X | >125 | 61 | 33 |
| 47 | Thr (Bzl) | allyl | X | X | >125 | 46 | 45 |
| 48 | Thr (Bzl) | benzyl | X | X | >125 | 56 | 39 |
| 49 | Val | methyl | X | X | >125 | 77 | 15 |
| 50 | Val | ethyl | X | X | >125 | 76 | 13 |
| 51 | Val | allyl | X | X | >125 | 60 | 24 |
| 52 | Val | benzyl | X | X | >125 | 56 | 18 |
| 53 | Trp (CHO) | methyl | X | X | >125 | 66 | 16 |
| 54 | Trp (CHO) | ethyl | X | X | >125 | 59 | 29 |
| 55 | Trp (CHO) | allyl | X | X | >125 | 50 | 26 |
| 56 | Trp (CHO) | benzyl | X | X | 121.7 | 49 | 18 |
| 57 | Tyr (Brz) | methyl | X | X | >125 | 88 | 6 |
| 58 | Tyr (Brz) | ethyl | X | X | >125 | 51 | 22 |
| 59 | Tyr (Brz) | allyl | X | X | >125 | 58 | 10 |
| 60 | Tyr (Brz) | benzyl | X | X | >125 | 49 | 11 |
| 61 | Tyr (ClBzl) | methyl | X | X | >125 | 74 | 0 |
| 62 | Tyr (ClBzl) | ethyl | X | X | >125 | 71 | 0 |
| 63 | Tyr (ClBzl) | allyl | X | X | >125 | 56 | 10 |
| 64 | Tyr (ClBzl) | benzyl | X | X | >125 | 60 | 5 |
| 65 | ala* | methyl | X | X | >125 | 51 | 25 |
| 66 | ala* | ethyl | X | X | >125 | 57 | 20 |
| 67 | ala* | allyl | X | X | >125 | 54 | 31 |
| 68 | ala* | benzyl | X | X | >125 | 60 | 17 |
| 69 | phe | methyl | X | X | >125 | 78 | 3 |
| 70 | phe | ethyl | X | X | >125 | 55 | 13 |
| 71 | phe | allyl | X | X | >125 | 55 | 11 |
| 72 | phe | benzyl | X | X | 117.7 | 48 | 7 |
| 73 | ile | methyl | X | X | >125 | 65 | 8 |
| 74 | ile | ethyl | X | X | >125 | 77 | 22 |
| 75 | ile | allyl | X | X | >125 | 60 | 24 |
| 76 | ile | benzyl | X | X | >125 | 72 | 15 |
| 77 | lys (Clz) | methyl | X | X | 74.2 | 21 | 0 |
| 78 | lys (Clz) | ethyl | X | X | 70.0 | 8 | 0 |
| 79 | lys (Clz) | allyl | X | X | 60.1 | 5 | 0 |
| 80 | lys (Clz) | benzyl | X | X | 27.0 | 0 | 0 |
| 81 | leu | methyl | X | X | >125 | 77 | 14 |
| 82 | leu | ethyl | X | X | >125 | 79 | 22 |
| 83 | leu | allyl | X | X | >125 | 64 | 24 |
| 84 | leu | benzyl | X | X | >125 | 80 | 5 |
| 85 | asn | methyl | X | X | >125 | 70 | 11 |
| 86 | asn | ethyl | X | X | >125 | 67 | 9 |
| 87 | asn | allyl | X | X | >125 | 12 | 9 |
| 88 | asn | benzyl | X | X | >125 | 18 | 0 |
| 89 | gln | methyl | X | X | >125 | 74 | 12 |
| 90 | gln | ethyl | X | X | >125 | 77 | 16 |
| 91 | gln | allyl | X | X | >125 | 15 | 13 |
| 92 | gln | benzyl | X | X | 121.7 | 46 | 0 |
| 93 | arg (Tos) | methyl | X | X | 18.4 | 66 | 0 |
| 94 | arg (Tos) | ethyl | X | X | 17.5 | 45 | 0 |
| 95 | arg (Tos) | allyl | X | X | 15.0 | 17 | 5 |
| 96 | arg (Tos) | benzyl | X | X | 9.3 | 38 | 18 |
| 97 | ser (Bzl) | methyl | X | X | >125 | 72 | 31 |
| 98 | ser (Bzl) | ethyl | X | X | >125 | 75 | 42 |
| 99 | ser (Bzl) | allyl | X | X | >125 | 45 | 34 |
| 100 | ser (Bzl) | benzyl | X | X | >125 | 70 | 21 |
| 101 | thr (Bzl) | methyl | X | X | >125 | 88 | 14 |
| 102 | thr (Bzl) | ethyl | X | X | >125 | 75 | 18 |
| 103 | thr (Bzl) | allyl | X | X | >125 | 59 | 29 |
| 104 | thr (Bzl) | benzyl | X | X | >125 | 72 | 26 |
| 105 | val | methyl | X | X | >125 | 70 | 18 |
| 106 | val | ethyl | X | X | >125 | 64 | 22 |
| 107 | val | allyl | X | X | >125 | 61 | 28 |
| 108 | val | benzyl | X | X | >125 | 49 | 19 |
| 109 | tyr (Brz) | methyl | X | X | >125 | 67 | 4 |
| 110 | tyr (Brz) | ethyl | X | X | >125 | 68 | 14 |
| 111 | tyr (Brz) | allyl | X | X | >125 | 50 | 19 |
| 112 | tyr (Brz) | benzyl | X | X | >125 | 73 | 11 |
| 113 | tyr (ClBzl) | methyl | X | X | >125 | 67 | 3 |
| 114 | tyr (ClBzl) | ethyl | X | X | >125 | 73 | 6 |
| 115 | tyr (ClBzl) | allyl | X | X | >125 | 72 | 12 |
| 116 | tyr (ClBzl) | benzyl | X | X | >125 | 76 | 8 |
| 117 | α-Aba | methyl | X | X | >125 | 82 | 11 |
| 118 | α-Aba | ethyl | X | X | >125 | 68 | 9 |
| 119 | α-Aba | allyl | X | X | >125 | 42 | 14 |
| 120 | α-Aba | benzyl | X | X | >125 | 56 | 0 |
| 121 | γ-Aba | methyl | X | X | >125 | 59 | 6 |
| 122 | γ-Aba | ethyl | X | X | >125 | 86 | 14 |
| 123 | γ-Aba | allyl | X | X | >125 | 37 | 17 |

TABLE 9-continued

Assays Of The Alkylated Hydantoin Library (Positional Scanning Format)

| No. | R¹ | R² | R³ | R⁴ | AM | σ | κ |
|---|---|---|---|---|---|---|---|
| 124 | γ-Aba | benzyl | X | X | >125 | 29 | 11 |
| 125 | α-Aib | methyl | X | X | >125 | 91 | 19 |
| 126 | α-Aib | ethyl | X | X | >125 | 68 | 33 |
| 127 | α-Aib | allyl | X | X | >125 | 48 | 40 |
| 128 | α-Aib | benzyl | X | X | >125 | 62 | 6 |
| 129 | Nve | methyl | X | X | >125 | 70 | 30 |
| 130 | Nve | ethyl | X | X | >125 | 62 | 31 |
| 131 | Nve | allyl | X | X | >125 | 54 | 34 |
| 132 | Nve | benzyl | X | X | 123.8 | 56 | 21 |
| 133 | nve | methyl | X | X | >125 | 81 | 0 |
| 134 | nve | ethyl | X | X | >125 | 66 | 10 |
| 135 | nve | allyl | X | X | >125 | 51 | 27 |
| 136 | nve | benzyl | X | X | >125 | 54 | 17 |
| 137 | Nle | methyl | X | X | >125 | 72 | 22 |
| 138 | Nle | ethyl | X | X | 123.4 | 65 | 29 |
| 139 | Nle | allyl | X | X | >125 | 60 | 34 |
| 140 | Nle | benzyl | X | X | 99.2 | 60 | 17 |
| 141 | nle | methyl | X | X | >125 | 72 | 6 |
| 142 | nle | ethyl | X | X | >125 | 58 | 13 |
| 143 | nle | allyl | X | X | >125 | 56 | 16 |
| 144 | nle | benzyl | X | X | 82.7 | 48 | 11 |
| 145 | ε-Aca | methyl | X | X | >125 | 36 | 8 |
| 146 | ε-Aca | ethyl | X | X | >125 | 58 | 28 |
| 147 | ε-Aca | allyl | X | X | >125 | 26 | 18 |
| 148 | ε-Aca | benzyl | X | X | >125 | 17 | 21 |
| 149 | 7-Aha | methyl | X | X | >125 | 43 | 0 |
| 150 | 7-Aha | ethyl | X | X | >125 | 42 | 1 |
| 151 | 7-Aha | allyl | X | X | >125 | 23 | 11 |
| 152 | 7-Aha | benzyl | X | X | >125 | 9 | 8 |
| 153 | ε-Lys (Clz) | methyl | X | X | 63.9 | 19 | 6 |
| 154 | ε-Lys (Clz) | ethyl | X | X | >125 | 26 | 22 |
| 155 | ε-Lys (Clz) | allyl | X | X | >125 | 32 | 25 |
| 156 | ε-Lys (Clz) | benzyl | X | X | >125 | 15 | 7 |
| 157 | Orn (Cbz) | methyl | X | X | 107.6 | 55 | 3 |
| 158 | Orn (Cbz) | ethyl | X | X | 79.3 | 55 | 8 |
| 159 | Orn (Cbz) | allyl | X | X | 66.3 | 29 | 4 |
| 160 | Orn (Cbz) | benzyl | X | X | 24.6 | 0 | 0 |
| 161 | δ-Orn (Cbz) | methyl | X | X | 74.4 | 39 | 8 |
| 162 | δ-Orn (Cbz) | ethyl | X | X | >125 | 40 | 19 |
| 163 | δ-Orn (Cbz) | allyl | X | X | >125 | 40 | 19 |
| 164 | δ-Orn (Cbz) | benzyl | X | X | >125 | 10 | 4 |
| 165 | Phg | methyl | X | X | >125 | 72 | 0 |
| 166 | Phg | ethyl | X | X | >125 | 68 | 12 |
| 167 | Phg | allyl | X | X | >125 | 59 | 13 |
| 168 | Phg | benzyl | X | X | >125 | 56 | 11 |
| 169 | phg | methyl | X | X | >125 | 74 | 0 |
| 170 | phg | ethyl | X | X | >125 | 73 | 13 |
| 171 | phg | allyl | X | X | >125 | 61 | 15 |
| 172 | phg | benzyl | X | X | >125 | 63 | 4 |
| 173 | Nal | methyl | X | X | >125 | 60 | 5 |
| 174 | Nal | ethyl | X | X | >125 | 58 | 0 |
| 175 | Nal | allyl | X | X | 85.6 | 47 | 0 |
| 176 | Nal | benzyl | X | X | 58.4 | 33 | 1 |
| 177 | nal | methyl | X | X | 116.7 | 69 | 2 |
| 178 | nal | ethyl | X | X | >125 | 65 | 13 |
| 179 | nal | allyl | X | X | >125 | 57 | 8 |
| 180 | nal | benzyl | X | X | 123.4 | 62 | 6 |
| 181 | β-Ala | methyl | X | X | >125 | 65 | 25 |
| 182 | β-Ala | ethyl | X | X | >125 | 71 | 14 |
| 183 | β-Ala | allyl | X | X | >125 | 43 | 12 |
| 184 | β-Ala | benzyl | X | X | >125 | 23 | 6 |
| 185 | Cha | methyl | X | X | 108.4 | 52 | 15 |
| 186 | Cha | ethyl | X | X | >125 | 57 | 11 |
| 187 | Cha | allyl | X | X | 94.4 | 42 | 6 |
| 188 | Cha | benzyl | X | X | 65.1 | 40 | 6 |
| 189 | cha | methyl | X | X | 94.9 | 41 | 18 |
| 190 | cha | ethyl | X | X | 111.7 | 57 | 27 |
| 191 | cha | allyl | X | X | >125 | 57 | 25 |
| 192 | cha | benzyl | X | X | 86.2 | 64 | 20 |
| 193 | pCl-Phe | methyl | X | X | 115.8 | 58 | 0 |
| 194 | pCl-Phe | ethyl | X | X | >125 | 60 | 3 |
| 195 | pCl-Phe | allyl | X | X | 111.1 | 52 | 2 |
| 196 | pCl-Phe | benzyl | X | X | 105.9 | 48 | 4 |
| 197 | pCl-phe | methyl | X | X | >125 | 64 | 17 |
| 198 | pCl-phe | ethyl | X | X | >125 | 68 | 15 |
| 199 | pCl-phe | allyl | X | X | >125 | 64 | 32 |
| 200 | pCl-phe | benzyl | X | X | >125 | 70 | 14 |
| 201 | pNO₂-Phe | methyl | X | X | >125 | 59 | 10 |
| 202 | pNO₂-Phe | ethyl | X | X | >125 | 66 | 12 |
| 203 | pNO₂-Phe | allyl | X | X | >125 | 30 | 26 |
| 204 | pNO₂-Phe | benzyl | X | X | >125 | 62 | 26 |
| 205 | pNO₂-phe | methyl | X | X | >125 | 67 | 11 |
| 206 | pNO₂-phe | ethyl | X | X | >125 | 94 | 14 |
| 207 | pNO₂-phe | allyl | X | X | >125 | 37 | 13 |
| 208 | pNO₂-phe | benzyl | X | X | >125 | 62 | 19 |
| 209 | pI-Phe | methyl | X | X | >125 | 75 | 2 |
| 210 | pI-Phe | ethyl | X | X | >125 | 60 | 2 |
| 211 | pI-Phe | allyl | X | X | >125 | 60 | 3 |
| 212 | pI-Phe | benzyl | X | X | 97.0 | 57 | 2 |
| 213 | Tha | methyl | X | X | >125 | 92 | 4 |
| 214 | Tha | ethyl | X | X | >125 | 74 | 0 |
| 215 | Tha | allyl | X | X | >125 | 66 | 5 |
| 216 | Tha | benzyl | X | X | >125 | 67 | 9 |
| 217 | tha | methyl | X | X | >125 | 63 | 7 |
| 218 | tha | ethyl | X | X | >125 | 69 | 10 |
| 219 | tha | allyl | X | X | >125 | 62 | 11 |
| 220 | tha | benzyl | X | X | >125 | 78 | 4 |
| 221 | Pya | methyl | X | X | 35.6 | 89 | 5 |
| 222 | Pya | ethyl | X | X | 18.7 | 60 | 0 |
| 223 | Pya | allyl | X | X | 15.8 | 35 | 15 |
| 224 | Pya | benzyl | X | X | 5.7 | 34 | 4 |
| 225 | pya | methyl | X | X | 32.4 | 55 | 15 |
| 226 | pya | ethyl | X | X | 18.3 | 65 | 9 |
| 227 | pya | allyl | X | X | 14.4 | 45 | 12 |
| 228 | pya | benzyl | X | X | 9.2 | 46 | 4 |
| 229 | pF-Phe | methyl | X | X | >125 | 83 | 6 |
| 230 | pF-Phe | ethyl | X | X | >125 | 83 | 4 |
| 231 | pF-Phe | allyl | X | X | >125 | 77 | 7 |
| 232 | pF-Phe | benzyl | X | X | >125 | 80 | 5 |
| 233 | pF-phe | methyl | X | X | >125 | 88 | 4 |
| 234 | pF-phe | ethyl | X | X | >125 | 70 | 6 |
| 235 | pF-phe | allyl | X | X | >125 | 54 | 13 |
| 236 | pF-phe | benzyl | X | X | >125 | 71 | 8 |
| 237 | X | X | Ala | H** | >125 | 45 | 3 |
| 238 | X | X | Ala | methyl | >125 | 31 | 4 |
| 239 | X | X | Ala | benzyl | >125 | 12 | 10 |
| 240 | X | X | Phe | H | >125 | 19 | 0 |
| 241 | X | X | Phe | methyl | >125 | 22 | 2 |
| 242 | X | X | Phe | benzyl | >125 | 19 | 18 |
| 243 | X | X | Gly | H | >125 | 36 | 13 |
| 244 | X | X | Gly | methyl | >125 | 27 | 15 |
| 245 | X | X | Gly | benzyl | >125 | 22 | 6 |
| 246 | X | X | Ile | H | >125 | 29 | 0 |
| 247 | X | X | Ile | methyl | >125 | 14 | 6 |
| 248 | X | X | Ile | benzyl | >125 | 4 | 15 |
| 249 | X | X | Lys (Boc) | H | >125 | 32 | 0 |
| 250 | X | X | Lys (Boc) | methyl | 115.0 | 25 | 3 |
| 251 | X | X | Lys (Boc) | benzyl | 51.5 | 28 | 3 |
| 252 | X | X | Leu | H | >125 | 27 | 0 |
| 253 | X | X | Leu | methyl | >125 | 16 | 1 |
| 254 | X | X | Leu | benzyl | >125 | 7 | 17 |
| 255 | X | X | Met (O) | H | >125 | 24 | 36 |
| 256 | X | X | Met (O) | methyl | 84.9 | 19 | 29 |
| 257 | X | X | Met (O) | benzyl | 39.6 | 15 | 22 |
| 258 | X | X | Asn (Trt) | H | >125 | 51 | 32 |
| 259 | X | X | Asn (Trt) | methyl | >125 | 48 | 32 |
| 260 | X | X | Asn (Trt) | benzyl | >125 | 65 | 41 |
| 261 | X | X | Gln (Trt) | H | >125 | 58 | 26 |
| 262 | X | X | Gln (Trt) | methyl | >125 | 48 | 27 |
| 263 | X | X | Gln (Trt) | benzyl | >125 | 43 | 10 |
| 264 | X | X | Arg (Pmc) | H | 61.0 | 52 | 4 |
| 265 | X | X | Arg (Pmc) | methyl | >125 | 34 | 21 |
| 266 | X | X | Arg (Pmc) | benzyl | 17.4 | 23 | 5 |
| 267 | X | X | Ser (tBu) | H | >125 | 53 | 43 |
| 268 | X | X | Ser (tBu) | methyl | >125 | 25 | 24 |
| 269 | X | X | Ser (tBu) | benzyl | >125 | 23 | 14 |

TABLE 9-continued

Assays Of The Alkylated Hydantoin Library (Positional Scanning Format)

| No. | $R^1$ | $R^2$ | $R^3$ | $R^4$ | AM | σ | κ |
|---|---|---|---|---|---|---|---|
| 270 | X | X | Thr (tBu) | H | >125 | 53 | 13 |
| 271 | X | X | Thr (tBu) | methyl | >125 | 16 | 2 |
| 272 | X | X | Thr (tBu) | benzyl | >125 | 29 | 9 |
| 273 | X | X | Val | H | >125 | 39 | 5 |
| 274 | X | X | Val | methyl | >125 | 19 | 11 |
| 275 | X | X | Val | benzyl | >125 | 9 | 15 |
| 276 | X | X | Trp (Boc) | H | >125 | 36 | 5 |
| 277 | X | X | Trp (Boc) | methyl | >125 | 30 | 3 |
| 278 | X | X | Trp (Boc) | benzyl | >125 | 26 | 10 |
| 279 | X | X | Trp | H | >125 | 39 | 11 |
| 280 | X | X | Trp | methyl | >125 | 27 | 4 |
| 281 | X | X | Trp | benzyl | >125 | 24 | 5 |
| 282 | X | X | Tyr (tBu) | H | >125 | 33 | 2 |
| 283 | X | X | Tyr (tBu) | methyl | >125 | 40 | 9 |
| 284 | X | X | Tyr (tBu) | benzyl | >125 | 32 | 7 |
| 285 | X | X | Tyr (Brz) | H | >125 | 36 | 3 |
| 286 | X | X | Tyr (Brz) | methyl | >125 | 23 | 2 |
| 287 | X | X | Tyr (Brz) | benzyl | >125 | 25 | 3 |
| 288 | X | X | ala | H | >125 | 30 | 0 |
| 289 | X | X | ala | methyl | >125 | 22 | 0 |
| 290 | X | X | ala | benzyl | >125 | 16 | 13 |
| 291 | X | X | phe | H | >125 | 27 | 2 |
| 292 | X | X | phe | methyl | >125 | 27 | 0 |
| 293 | X | X | phe | benzyl | >125 | 13 | 8 |
| 294 | X | X | ile | H | >125 | 29 | 15 |
| 295 | X | X | ile | methyl | >125 | 13 | 11 |
| 296 | X | X | ile | benzyl | >125 | 5 | 11 |
| 297 | X | X | lys (Boc) | H | >125 | 28 | 13 |
| 298 | X | X | lys (Boc) | methyl | >125 | 42 | 22 |
| 299 | X | X | lys (Boc) | benzyl | 38.2 | 20 | 16 |
| 300 | X | X | leu | H | >125 | 30 | 16 |
| 301 | X | X | leu | methyl | >125 | 14 | 0 |
| 302 | X | X | leu | benzyl | >125 | 7 | 12 |
| 303 | X | X | asn (Trt) | H | >125 | 46 | 34 |
| 304 | X | X | asn (Trt) | methyl | >125 | 44 | 28 |
| 305 | X | X | asn (Trt) | benzyl | >125 | 35 | 26 |
| 306 | X | X | gln (Trt) | H | >125 | 51 | 40 |
| 307 | X | X | gln (Trt) | methyl | >125 | 50 | 30 |
| 308 | X | X | gln (Trt) | benzyl | >125 | 42 | 18 |
| 309 | X | X | ser (Bzl) | H | >125 | 52 | 25 |
| 310 | X | X | ser (Bzl) | methyl | >125 | 28 | 15 |
| 311 | X | X | ser (Bzl) | benzyl | >125 | 25 | 18 |
| 312 | X | X | thr (Bzl) | H | >125 | 42 | 21 |
| 313 | X | X | thr (Bzl) | methyl | >125 | 20 | 18 |
| 314 | X | X | thr (Bzl) | benzyl | >125 | 30 | 12 |
| 315 | X | X | val | H | >125 | 42 | 7 |
| 316 | X | X | val | methyl | >125 | 18 | 4 |
| 317 | X | X | val | benzyl | >125 | 7 | 6 |
| 318 | X | X | trp (Boc) | H | >125 | 38 | 1 |
| 319 | X | X | trp (Boc) | methyl | >125 | 31 | 3 |
| 320 | X | X | trp (Boc) | benzyl | >125 | 75 | 18 |
| 321 | X | X | trp | H | >125 | 44 | 8 |
| 322 | X | X | trp | methyl | >125 | 26 | 12 |
| 323 | X | X | trp | benzyl | >125 | 26 | 6 |
| 324 | X | X | tyr (tBu) | H | >125 | 49 | 3 |
| 325 | X | X | tyr (tBu) | methyl | >125 | 43 | 6 |
| 326 | X | X | tyr (tBu) | benzyl | >125 | 22 | 4 |
| 327 | X | X | arg (Pmc) | H | 86.1 | 19 | 10 |
| 328 | X | X | arg (Pmc) | methyl | 37.5 | 32 | 0 |
| 329 | X | X | arg (Pmc) | benzyl | 17.2 | 15 | 6 |
| 330 | X | X | Nle | H | >125 | 24 | 0 |
| 331 | X | X | Nle | methyl | >125 | 13 | 4 |
| 332 | X | X | Nle | benzyl | 107.7 | 11 | 5 |
| 333 | X | X | nle | H | >125 | 30 | 0 |
| 334 | X | X | nle | methyl | >125 | 11 | 0 |
| 335 | X | X | nle | benzyl | 98.0 | 7 | 0 |
| 336 | X | X | Nve | H | >125 | 28 | 0 |
| 337 | X | X | Nve | methyl | >125 | 19 | 0 |
| 338 | X | X | Nve | benzyl | >125 | 8 | 3 |
| 339 | X | X | nve | H | >125 | 36 | 0 |
| 340 | X | X | nve | methyl | >125 | 23 | 0 |
| 341 | X | X | nve | benzyl | >125 | 11 | 11 |
| 342 | X | X | Nal | H | >125 | 12 | 8 |
| 343 | X | X | Nal | methyl | >125 | 13 | 0 |
| 344 | X | X | Nal | benzyl | >125 | 6 | 6 |
| 345 | X | X | nal | H | >125 | 22 | 12 |
| 346 | X | X | nal | methyl | 100.3 | 17 | 20 |
| 347 | X | X | nal | benzyl | 98.0 | 14 | 30 |
| 348 | X | X | Phg | H | >125 | 35 | 38 |
| 349 | X | X | Phg | methyl | >125 | 22 | 15 |
| 350 | X | X | Phg | benzyl | >125 | 10 | 18 |
| 351 | X | X | Glu (tBu) | H | >125 | 40 | 33 |
| 352 | X | X | Glu (tBu) | methyl | >125 | 43 | 38 |
| 353 | X | X | Glu (tBu) | benzyl | >125 | 38 | 23 |
| 354 | X | X | glu (tBu) | H | >125 | 39 | 34 |
| 355 | X | X | glu (tBu) | methyl | >125 | 47 | 48 |
| 356 | X | X | glu (tBu) | benzyl | >125 | 38 | 33 |
| 357 | X | X | Cha | H | >125 | 14 | 0 |
| 358 | X | X | Cha | methyl | 95.5 | 9 | 12 |
| 359 | X | X | Cha | benzyl | 81.6 | 6 | 10 |
| 360 | X | X | cha | H | 103.6 | 8 | 6 |
| 361 | X | X | cha | methyl | 82.9 | 7 | 16 |
| 362 | X | X | cha | benzyl | 57.1 | 8 | 18 |
| 363 | X | X | pCl-Phe | H | 117.0 | 16 | 20 |
| 364 | X | X | pCl-Phe | methyl | 103.3 | 25 | 32 |
| 365 | X | X | pCl-Phe | benzyl | 63.5 | 11 | 8 |
| 366 | X | X | pCl-phe | H | 105.1 | 20 | 10 |
| 367 | X | X | pCl-phe | methyl | 101.6 | 20 | 16 |
| 368 | X | X | pCl-phe | benzyl | 66.2 | 7 | 18 |
| 369 | X | X | pya | H | >125 | 52 | 30 |
| 370 | X | X | pya | methyl | 15.0 | 28 | 19 |
| 371 | X | X | pya | benzyl | 9.4 | 17 | 24 |

*lower case lettering indicates D-amino acids
**"H" stands for hydrogen atom

EXAMPLE VII

This example provides the synthesis of individual tri-alkylated hydantoins of the present invention; (1) X=O. One first Boc protected amino acid provided in Table 10 was used, generating one $R^1$ group. One alkyl halide was used to generate the $R^2$ group in the initial alkylation which as summarized in Table 10 below. Two second Fmoc protected amino acids were used to generate the $R^3$ groups, which amino acids are also summarized in Table 10 below. Also provided in the Table below, two $R^4$ groups were generated were by performing a second alkylation with two alkyl halides and two $R^5$ groups were generated by performing a third alkylation with two alkyl halides. Therefore, Table 10 provides a summary of all the amino acids ($R^1$ and $R^3$) and alkyl groups ($R^2$, $R^4$ and $R^5$) used in the preparation of the tri-alkylated compounds.

TABLE 10

SUMMARY OF R GROUPS IN INDIVIDUAL TRIALKYLATED HYDANTOINS

| | $R^1$ | $R^2$ | $R^3$ | $R^4$ | $R^5$ |
|---|---|---|---|---|---|
| 1 | Phe | methyl | Phe | methyl | methyl |
| 2 | | | Val | benzyl | benzyl |

A typical procedure for the synthesis of the subject tri-alkylated hydantoins was as follows. One hundred mg of p-methylbenzhydrylamine (MBHA) resin (0.81 meq/g, 100–200 mesh) was contained within a sealed polypropylene mesh packet. Reactions were carried out in a 10 ml polyethylene bottle. Following neutralization with 5% diisopropylethylamine (DIEA) in dichloromethane (DCM), the resin was washed with DCM. The first Boc-protected amino acid (protected amino acid in FIG. 1) was coupled using the conventional reagents hydroxybenzotriazole (HOBt) and diisopropylcarbodiimide (DICI) under the conditions described in Example I. The Boc protecting group was then removed with 55% TFA in $CH_2Cl_2$. Following neutralization with 5% diisopropylethylamine (DIEA) in dichloromethane (DCM) and was washing with DCM, the mesh packet was shaken overnight in a solution of trityl chloride in DCM/DMF (9:1) in the presence of DIEA. Completeness of the trityl coupling was verified using the bromophenol blue color test as described in Krchnak et al. *Coll. Czech. Chem. Commun.*, 53:2542 (1988), which is incorporated herein by reference.

N-alkylation was then performed by treatment of the resin packet with 1M lithium t-butoxide in THF. Excess base was removed by cannulation, followed by addition of the individual alkylating agent in DMSO. The solution was vigorously shaken for 2 h at room temperature. Upon removal of the trityl group with 2% TFA in DCM (2×10 min), the packet was washed, neutralized and the second Fmoc-protected amino acid (protected amino acid in FIG. 1) coupled under the conditions described in Example I.

Following removal of the Fmoc group, hydantoins were formed following treatment for fifteen minutes with a 24-fold excess of triphosgene (0.1M in dichloromethane anhydrous with a 5-fold excess of DIEA over resin substitution). The solution was then removed, the resin washed with dry dichloromethane. Dry dichloromethane was added and the resin shaken for 12 hours to allow the cyclization to go to completion, followed by washing with dichloromethane.

N-alkylation was then performed by treatment of the resin packet with 1M sodium cyclopentadienylide in THF. Excess base was removed by cannulation, followed by addition of the individual alkylating agent in DMSO. The solution was vigorously shaken for 2 h at room temperature, followed by decantation and washing.

C-alkylation was then performed by treatment of the resin packet with 1M sodium lithium tert-butoxide in THF. Excess base was removed by cannulation, followed by addition of the individual alkylating agent in DMSO. The solution was vigorously shaken for 2 h at room temperature, followed by decantation and washing.

Following cleavage from the resin with anhydrous HF by the procedures of Houghten et al. *Int. J. Pep. Prot. Res.*, 27:673 (1986), which is incorporated herein by reference, in the presence of anisole, the desired products were extracted and lyophilized. The desired products were obtained in good yields and high purity following lyophilization.

EXAMPLE VIII

Following the procedures of Example VII, the following tri-alkylated hydantoin pools were prepared. Therefore, X=O the R groups and their respective reference numbers are identified in Table 11 below.

TABLE 11

REFERENCE NUMBERS AND FOR VARIABLE R GROUPS FOR TRIALKYLATED HYDANTOINS

| Pool No. | $R^1$ | $R^2$ | $R^3$ | $R^4$ | $R^5$ |
|---|---|---|---|---|---|
| 1 | Phe | methyl | Val | methyl | methyl |
| 2 | Phe | methyl | Val | benzyl | benzyl |
| 3 | Phe | methyl | Phe | methyl | methyl |
| 4 | Phe | methyl | Phe | benzyl | benzyl |

All journal article and reference citations provided above, in parentheses or otherwise, whether previously stated or not, are incorporated herein by reference.

Although the invention has been described with reference to the examples provided above, it should be understood that various modifications can be made without departing from the spirit of the inventions. Accordingly the invention is limited only by the claims.

We claim:

1. A composition of matter, comprising a combinatorial library of two or more hydantoin compounds comprising the structure:

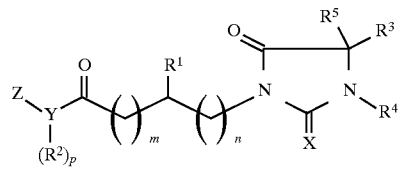

wherein:

$R^1$ is selected from the group consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, amino, (monosubstituted) amino, (disubstituted)amino, (trisubstituted)amino, carboxy, substituted carboxy, carbamoyl, substituted carbamoyl, $C_3$ to $C_7$ cycloalkyl, and $C_3$ to $C_7$ substituted cycloalkyl;

$R^2$ is selected from the group consisting of a hydrogen atom, $C_1$ to $C_{10}$ alkyl, $C_2$ to $C_{10}$ alkenyl, benzyl, substituted benzyl, naphthylmethyl, and substituted naphthylmethyl;

$R^3$ is selected from the group consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;

$R^4$ is selected from the group consisting of a hydrogen atom, $C_1$ to $C_{10}$ alkyl, $C_2$ to $C_{10}$ alkenyl, benzyl, substituted benzyl, naphthylmethyl, and substituted naphthylmethyl;

$R^5$ is selected from the group consisting of a hydrogen atom, $C_1$ to $C_{10}$ alkyl, $C_2$ to $C_{10}$ alkenyl, benzyl, substituted benzyl, naphthylmethyl, and substituted naphthylmethyl;

X is selected from the group consisting of an oxygen atom(O) and a sulfur atom(S);

Y is selected from the group consisting of a nitrogen atom (N) and an oxygen atom (O);

Z is selected from the group consisting of hydrogen, an amino resin, and a hydroxy resin;

m is zero to five;

n is zero to four; and p is zero or one, provided that when Y is nitrogen, p is one and Z is hydrogen or an amino resin and further provided that when Y is oxygen p is zero and Z is hydrogen or a hydroxy resin.

2. The composition of claim 1, wherein $R^2$, $R^4$, and $R^5$ are, independently, selected from the group consisting of a hydrogen atom, methyl, ethyl, benzyl, allyl, and naphthylmethyl and further wherein Y is a nitrogen atom.

3. The composition of claim 2, wherein $R^2$, $R^4$ and $R^5$ are, independently, a hydrogen atom and Y is a nitrogen atom.

4. The composition of any one of claims 1, 2, or 3, wherein X is an oxygen atom.

5. The composition of any one of claims 1, 2, or 3, wherein X is a sulfur atom.

6. The composition of claim 1, wherein:

$R^1$ is selected from the group consisting of methyl, benzyl, a hydrogen atom, 2-butyl, aminobutyl, 2-methylpropyl, methylthioethyl, carbamoylmethyl, carbamoylethyl, guanidinopropyl, hydroxymethyl, 1-hydroxyethyl, 2-propyl, 3-indolylmethyl, 4-hydroxybenzyl, 4-chlorobenzyl, ethyl, dimethyl, propyl, butyl, amino, aminopropyl, phenyl, 2-naphthylmethyl, cyclohexylmethyl, 4-nitrobenzyl, cyclohexyl, 4-iodobenzyl, t-butyl, acetamidobutyl, 4-fluorobenzyl, thiomethyl, carboxymethyl, carboxyethyl, N-(2,4-dinitrophenyl)-4-imidazolylmethyl, 2-thienylmethyl, 3-pyridylmethyl, 4-benzoylbenzyl, 4-fluorenylmethyloxycarbonylaminobenzyl, fluorenylmethyloxycarbonylmethyl, 4-ethoxybenzyl, fluorenylmethyloxycarbonylamino, fluorenylmethyloxycarbonylaminopropyl, fluorenylmethyloxycarbonylaminobutyl, and fluorenylmethyloxycarbonylethyl;

$R^2$ is a hydrogen atom;

$R^3$ is selected from the group consisting of methyl, benzyl, a hydrogen atom, 2-butyl, aminobutyl, 2-methylpropyl, methylthioethyl, guanidinopropyl, hydroxymethyl, 1-hydroxyethyl, 2-propyl, 3-indolylmethyl, 4-hydroxybenzyl, ethyl, dimethyl, propyl, butyl, aminopropyl, phenyl, 2-naphthylmethyl, cyclohexylmethyl, 4-nitrobenzyl, cyclohexyl, 4-iodobenzyl, 4-chlorobenzyl, t-butyl, acetamidobutyl, 4-fluorobenzyl, thiomethyl, carboxymethyl, carboxyethyl, N-(2,4-dinitrophenyl)-4-imidazolylmethyl, 2-thienylmethyl, 3-pyridylmethyl, 4-benzoylbenzyl, fluorenylmethyloxycarbonylmethyl, 4-ethoxybenzyl, fluorenylmethyloxycarbonylaminopropyl, fluorenylmethyloxycarbonylaminobutyl, fluorenylmethyloxycarbonylethyl, 4-fluorenylmethyloxycarbonylaminobenzyl, and 4-imidazolylmethyl;

$R^4$ is a hydrogen atom;

$R^5$ is a hydrogen atom;

X is an oxygen atom;

Y is a nitrogen atom;

m is zero to five; and n is zero to four.

7. The composition of claim 1, wherein:

$R^1$ is selected from the group consisting of methyl, carboxymethyl, carboxyethyl, benzyl, a hydrogen atom, N-(2,4-dinitrophenyl)-4-imidazolylmethyl, 2-butyl, aminobutyl, 2-methylpropyl, methylsulfinylethyl, carbamoylmethyl, carbamoylethyl, guanidinopropyl, hydroxymethyl, 1-hydroxyethyl, 2-propyl, N-formyl-3-indolylmethyl, 4-hydroxybenzyl, ethyl, propyl, butyl, aminopropyl, amino, phenyl, 2-naphthylmethyl, cyclohexylmethyl, fluorenylmethyloxycarbonylaminobutyl, methylsulfonylethyl, 4-nitrobenzyl, 4-chlorobenzyl, 4-fluorobenzyl, acetamidobutyl, 3-pyridylmethyl, 2-thienylmethyl, t-butyl, 4-ethoxybenzyl, 4-fluorenylmethyloxycarbonylaminobenzyl, 3-indolylmethyl, fluorenylmethyloxycarbonylmethyl, 4-benzoylbenzyl, 4-iodobenzyl, cyclohexyl, fluorenylmethyloxycarbonylaminopropyl, fluorenylmethyloxycarbonylaminopropyl, fluorenylmethyloxycarbonylethyl, 4-imidazolylmethyl, dimethyl, amino, carboxy, fluorenylmethyloxycarbonylamino, carbamoyl, and fluorenylmethyloxycarbonyl;

$R^2$ is a hydrogen atom;

$R^3$ is selected from the group consisting of methyl, carboxymethyl, carboxyethyl, benzyl, a hydrogen atom, N-(2,4-dinitrophenyl)-4-imidazolylmethyl, 2-butyl, aminobutyl, 2-methylpropyl, methylsulfinylethyl, carbamoylmethyl, carbamoylethyl, guanidinopropyl, hydroxymethyl, 1-hydroxyethyl, 2-propyl, N-formyl-3-indolylmethyl, 4-hydroxybenzyl, ethyl, propyl, butyl, aminopropyl, phenyl, 2-naphthylmethyl, cyclohexylmethyl, fluorenylmethyloxycarbonylaminobutyl, methylsulfonylethyl, 4-nitrobenzyl, 4-chlorobenzyl, 4-fluorobenzyl, acetamidobutyl, 3-pyridylmethyl, 2-thienylmethyl, t-butyl, 4-ethoxybenzyl, 4-fluorenylmethyloxycarbonylaminobenzyl, 3-indolylmethyl, fluorenylmethyloxycarbonylmethyl, 4-benzoylbenzyl, 4-iodobenzyl, cyclohexyl, fluorenylmethyloxycarbonylaminopropyl, fluorenylmethyloxycarbonylaminopropyl, fluorenylmethyloxycarbonylethyl, or 4-imidazolylmethyl;

$R^4$ is a hydrogen atom;

$R^5$ is a hydrogen atom;

X is a sulfur atom;

Y is a nitrogen atom;

m is zero to five; and n is zero to four.

8. The composition of claim 1, wherein:

$R^1$ is selected from the group consisting of methyl, benzyl, a hydrogen atom, 2-butyl, methylaminobutyl, ethylaminobutyl, allylaminobutyl, benzylaminobutyl, 2-methylpropyl, methylsulfinylethyl, dimethylcarbamoylmethyl, diethylcarbamoylmethyl, diallylcarbamoylmethyl, dibenzylcarbamoylmethyl, dimethylcarbamoylethyl, diethylcarbamoylethyl, diallylcarbamoylethyl, dibenzylcarbamoylethyl, trimethylguanidinopropyl, triethylguanidinopropyl, triallylguanidinopropyl, benzylguanidinopropyl, dibenzylguanidinopropyl, hydroxymethyl, 1-hydroxyethyl, 2-propyl, N-methyl-3-indolylmethyl, N-ethyl-3-indolylmethyl, N-allyl-3-indolylmethyl, N-benzyl-3-indolylmethyl, 4-hydroxybenzyl, 4-methoxybenzyl, 4-ethoxybenzyl, 4-alloxybenzyl, ethyl, dimethyl, propyl, butyl, methylamino, ethylamino, allylamino, benzylamino, methylaminopropyl, ethylaminopropyl, allylaminopropyl, benzylaminopropyl, phenyl, 2-naphthylmethyl, cyclohexylmethyl, 4-chlorobenzyl, 4-nitrobenzyl, 4-iodobenzyl, 1-methyl-thien-2-ylmethyl, 1-ethyl-thien-2-ylmethyl, 1-allyl-thien-2-ylmethyl, 1-benzyl-thien-2-ylmethyl, 1-methyl-pyrid-3-ylmethyl, 1-ethyl-pyrid-3-ylmethyl, 1-allyl-pyrid-3-ylmethyl, 1-benzyl-pyrid-3-ylmethyl, and 4-fluorobenzyl;

$R^2$ is selected from the group consisting of methyl, ethyl, allyl, and benzyl;

$R^3$ is selected from the group consisting of methyl, benzyl, a hydrogen atom, 2-butyl, aminobutyl, methylaminobutyl, benzylaminobutyl, 2-methylpropyl, methylsulfinylethyl, carbamoylmethyl, carbamoylethyl, guanidinopropyl, trimethylguanidinopropyl, benzylguanidinopropyl, dibenzylguanidinopropyl, hydroxymethyl, 1-hydroxyethyl, 2-propyl, 3-indolylmethyl, N-methyl-3-indolylmethyl, N-benzyl-3-indolylmethyl, 4-hydroxybenzyl, 4-methoxybenzyl, propyl, butyl, phenyl, 2-naphthylmethyl, carboxyethyl, cyclohexylmethyl, 4-chlorobenzyl, 1-methyl-pyrid-3-ylmethyl, 1-ethyl-pyrid-3-ylmethyl, 1-allyl-pyrid-3-ylmethyl, and 1-benzyl-pyrid-3-ylmethyl;

$R^4$ is selected from the group consisting of a hydrogen atom, methyl, and benzyl;

$R_5$ is a hydrogen atom;

X is an oxygen atom;

Y is a nitrogen atom;

m is zero to five; and n is zero to four.

9. The composition of claim 1, wherein Z is a hydrogen atom.

10. A single hydantoin compound comprising the structure:

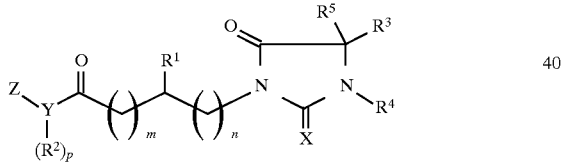

$R^1$ is selected from the group consisting of $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, amino, (monosubstituted) amino, (disubstituted)amino, (trisubstituted)amino, carboxy, substituted carboxy, carbamoyl, $C_3$ to $C_7$ cycloalkyl, and $C_3$ to $C_7$ substituted cycloalkyl;

$R^2$ is selected from the group consisting of a hydrogen atom, $C_1$ to $C_{10}$ alkyl, $C_2$ to $C_{10}$ alkenyl, benzyl, substituted benzyl, naphthylmethyl, and substituted naphthylmethyl;

$R^3$ is selected from the group consisting of a hydrogen atom, $C_1$ to $C_{10}$ alkyl, $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl, provided that, where $C_1$ to $C_{10}$ substituted alkyl is selected and the substitution is with a protected carboxy, the carboxy-protecting group is selected from the group consisting of 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4', 4"-trimethoxytrityl, 2-phenylprop-2-yl, trimethylsilyl, t-butyldimethylsilyl, 2,2,2-trichloroethyl, β-(trimethylsilyl)ethyl, β-(di(n-butyl)methylsilyl)ethyl, p-toluenesulfonylethyl, 4-nitrobenzyl-sulfonylethyl, allyl, cinnamyl, and 1-(trimethylsilylmethyl)-prop-1-en-3-yl;

$R^4$ is selected from the group consisting of a hydrogen atom, $C_1$ to $C_{10}$ alkyl, $C_2$ to $C_{10}$ alkenyl, benzyl, substituted benzyl, naphthylmethyl, and substituted naphthylmethyl;

$R^5$ is selected from the group consisting of a hydrogen atom, $C_1$ to $C_{10}$ alkyl, $C_2$ to $C_{10}$ alkenyl, benzyl, substituted benzyl, naphthylmethyl, and substituted naphthylmethyl;

X is selected from the group consisting of an oxygen atom(O) and a sulfur atom(S);

Y is a nitrogen atom (N);

Z is a hydrogen atom;

m is zero to five;

n is zero to four; and p is one, or a pharmaceutically-acceptable salt thereof.

11. The compound of claim 10, wherein $R^2$, $R^4$ and $R^5$ are, independently, selected from the group consisting of a hydrogen atom, methyl, ethyl, benzyl, allyl, and naphthylmethyl and further provided that Y is a nitrogen atom.

12. The compound of claim 11, wherein $R^2$, $R^4$ and $R^5$ are, independently, a hydrogen atom and Y is a nitrogen atom.

13. The compound of any one of claims 10, 11 or 12, wherein X is an oxygen atom.

14. The compound of any one of claims 10, 11 or 12, wherein X is a sulfur atom.

15. The compound of claim 10, wherein:

$R_1$ is selected from the group consisting of methyl, benzyl, 2-butyl, aminobutyl, 2-methylpropyl, methylthioethyl, carbamoylmethyl, carbamoylethyl, guanidinopropyl, hydroxymethyl, 1-hydroxyethyl, 2-propyl, 3-indolylmethyl, 4-hydroxybenzyl, 4-chlorobenzyl, ethyl, dimethyl, propyl, butyl, amino, aminopropyl, phenyl, 2-naphthylmethyl, cyclohexylmethyl, 4-nitrobenzyl, cyclohexyl, 4-iodobenzyl, t-butyl, acetamidobutyl, 4-fluorobenzyl, thiomethyl, carboxymethyl, carboxyethyl, N-(2,4-dinitrophenyl)-4-imidazolylmethyl, 2-thienylmethyl, 3-pyridylmethyl, 4-benzoylbenzyl, 4-fluorenylmethyloxycarbonylaminobenzyl, fluorenylmethyloxycarbonylmethyl, 4-ethoxybenzyl, fluorenylmethyloxycarbonylamino, fluorenylmethyloxycarbonylaminopropyl, fluorenylmethyloxycarbonylaminobutyl, and fluorenylmethyloxycarbonylethyl;

$R^2$ is a hydrogen atom;

$R^3$ is selected from the group consisting of methyl, benzyl, a hydrogen atom, 2-butyl, aminobutyl, 2-methylpropyl, methylthioethyl, guanidinopropyl, hydroxymethyl, 1-hydroxyethyl, 2-propyl, 3-indolylmethyl, 4-hydroxybenzyl, ethyl, dimethyl, propyl, butyl, aminopropyl, phenyl, 2-naphthylmethyl, cyclohexylmethyl, 4-nitrobenzyl, cyclohexyl, 4-iodobenzyl, 4-chlorobenzyl, t-butyl, acetamidobutyl, 4-fluorobenzyl, thiomethyl, carboxymethyl, carboxyethyl, N-(2,4-dinitrophenyl)-4-imidazolylmethyl, 2-thienylmethyl, 3-pyridylmethyl,

47

4-benzoylbenzyl, fluorenylmethyloxycarbonylmethyl, 4-ethoxybenzyl, fluorenylmethyloxycarbonylaminopropyl, fluorenylmethyloxycarbonylaminobutyl, fluorenylmethyloxycarbonylethyl, 4-fluorenylmethyloxycarbonylaminobenzyl, and 4-imidazolylmethyl;

$R^4$ is a hydrogen atom;

$R^5$ is a hydrogen atom;

X is an oxygen atom;

Y is a nitrogen atom;

m is zero to five; and n is zero to four.

16. The compound of claim 10, wherein:

$R^1$ is selected from the group consisting of methyl, carboxymethyl, carboxyethyl, benzyl, N-(2,4-dinitrophenyl)-4-imidazolylmethyl, 2-butyl, aminobutyl, 2-methylpropyl, methylsulfinylethyl, carbamoylmethyl, carbamoylethyl, guanidinopropyl, hydroxymethyl, 1-hydroxyethyl, 2-propyl, N-formyl-3-indolylmethyl, 4-hydroxybenzyl, ethyl, propyl, butyl, aminopropyl, amino, phenyl, 2-naphthylmethyl, cyclohexylmethyl, fluorenylmethyloxycarbonylaminobutyl, methylsulfonylethyl, 4-nitrobenzyl, 4-chlorobenzyl, 4-fluorobenzyl, acetamidobutyl, 3-pyridylmethyl, 2-thienylmethyl, t-butyl, 4-ethoxybenzyl, 4-fluorenylmethyloxycarbonylaminobenzyl, 3-indolylmethyl, fluorenylmethyloxycarbonylmethyl, 4-benzoylbenzyl, 4-iodobenzyl, cyclohexyl, fluorenylmethyloxycarbonylaminopropyl, fluorenylmethyloxycarbonylaminopropyl, fluorenylmethyloxycarbonylethyl, 4-imidazolylmethyl, dimethyl, amino, carboxy, fluorenylmethyloxycarbonylamino, carbamoyl, and fluorenylmethyloxycarbonyl;

$R^2$ is a hydrogen atom;

$R^3$ is selected from the group consisting of methyl, carboxymethyl, carboxyethyl, benzyl, a hydrogen atom, N-(2,4-dinitrophenyl)-4-imidazolylmethyl, 2-butyl, aminobutyl, 2-methylpropyl, methylsulfinylethyl, carbamoylmethyl, carbamoylethyl, guanidinopropyl, hydroxymethyl, 1-hydroxyethyl, 2-propyl, N-formyl-3-indolylmethyl, 4-hydroxybenzyl, ethyl, propyl, butyl, aminopropyl, phenyl, 2-naphthylmethyl, cyclohexylmethyl, fluorenylmethyloxycarbonylaminobutyl, methylsulfonylethyl, 4-nitrobenzyl, 4-chlorobenzyl, 4-fluorobenzyl, acetamidobutyl, 3-pyridylmethyl, 2-thienylmethyl, t-butyl, 4-ethoxybenzyl, 4-fluorenylmethyloxycarbonylaminobenzyl, 3-indolylmethyl, fluorenylmethyloxycarbonylmethyl, 4-benzoylbenzyl, 4-iodobenzyl, cyclohexyl, fluorenylmethyloxycarbonylaminopropyl, fluorenylmethyloxycarbonylaminopropyl, fluorenylmethyloxycarbonylethyl, and 4-imidazolylmethyl;

$R^4$ is a hydrogen atom;

$R^5$ is a hydrogen atom;

X is a sulfur atom(S);

Y is a nitrogen atom;

m is zero to five; and n is zero to four.

17. The compound of claim 10, wherein:

48

$R^1$ is selected from the group consisting of methyl, benzyl, 2-butyl, methylaminobutyl, ethylaminobutyl, allylaminobutyl, benzylaminobutyl, 2-methylpropyl, methylsulfinylethyl, dimethylcarbamoylmethyl, diethylcarbamoylmethyl, diallylcarbamoylmethyl, dibenzylcarbamoylmethyl, dimethylcarbamoylethyl, diethylcarbamoylethyl, diallylcarbamoylethyl, dibenzylcarbamoylethyl, trimethylguanidinopropyl, triethylguanidinopropyl, triallylguanidinopropyl, benzylguanidinopropyl, dibenzylguanidinopropyl, hydroxymethyl, 1-hydroxyethyl, 2-propyl, N-methyl-3-indolylmethyl, N-ethyl-3-indolylmethyl, N-allyl-3-indolylmethyl, N-benzyl-3-indolylmethyl, 4-hydroxybenzyl, 4-methoxybenzyl, 4-ethoxybenzyl, 4-alloxybenzyl, ethyl, dimethyl, propyl, butyl, methylamino, ethylamino, allylamino, benzylamino, methylaminopropyl, ethylaminopropyl, allylaminopropyl, benzylaminopropyl, phenyl, 2-naphthylmethyl, cyclohexylmethyl, 4-chlorobenzyl, 4-nitrobenzyl, 4-iodobenzyl, 1-methyl-thien-2-ylmethyl, 1-ethyl-thien-2-ylmethyl, 1-allyl-thien-2-ylmethyl, 1-benzyl-thien-2-ylmethyl, 1-methyl-pyrid-3-ylmethyl, 1-ethyl-pyrid-3-ylmethyl, 1-allyl-pyrid-3-ylmethyl, 1-benzyl-pyrid-3-ylmethyl, and 4-fluorobenzyl;

$R^2$ is selected from the group consisting of methyl, ethyl, allyl, and benzyl;

$R^3$ is selected from the group consisting of methyl, benzyl, a hydrogen atom, 2-butyl, aminobutyl, methylaminobutyl, benzylaminobutyl, 2-methylpropyl, methylsulfinylethyl, carbamoylmethyl, carbamoylethyl, guanidinopropyl, trimethylguanidinopropyl, benzylguanidinopropyl, dibenzylguanidinopropyl, hydroxymethyl, 1-hydroxyethyl, 2-propyl, 3-indolylmethyl, N-methyl-3-indolylmethyl, N-benzyl-3-indolylmethyl, 4-hydroxybenzyl, 4-methoxybenzyl, propyl, butyl, phenyl, 2-naphthylmethyl, carboxyethyl, cyclohexylmethyl, 4-chlorobenzyl, 1-methyl-pyrid-3-ylmethyl, 1-ethyl-pyrid-3-ylmethyl, 1-allyl-pyrid-3-ylmethyl, and 1-benzyl-pyrid-3-ylmethyl;

$R^4$ is selected from the group consisting of a hydrogen atom, methyl, and benzyl;

$R^5$ is a hydrogen atom;

X is an oxygen atom(O);

Y is a nitrogen atom;

m is zero to five; and n is zero to four.

18. A single thiohydantoin compound comprising the structure:

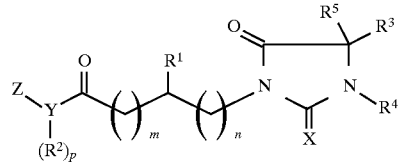

wherein:

$R^1$ is selected from the group consisting of a hydrogen atom, $C_1$ to $C_{10}$ alkyl; $C_1$ to $C_{10}$ substituted alkyl, $C_7$ to $C_{16}$ phenylalkyl, $C_7$ to $C_{16}$ substituted phenylalkyl, phenyl, substituted phenyl, amino, (monosubstituted) amino, (disubstituted)amino, (trisubstituted)amino, carboxy, substituted carboxy, carbamoyl, $C_3$ to $C_7$ cycloalkyl, and $C_3$ to $C_7$ substituted cycloalkyl;

$R^2$ is selected from the group consisting of a hydrogen atom, $C_1$ to $C_{10}$ alkyl, $C_2$ to $C_{10}$ alkenyl, benzyl, substituted benzyl, naphthylmethyl, and substituted naphthylmethyl;

$R^3$ is selected from the group consisting of a hydrogen atom, $C_1$ to $C_{10}$ alkyl; $C_1$ to $C_{10}$ substituted alkyl, $C_7$ to $C_{16}$ phenylalkyl, $C_7$ to $C_{16}$ substituted phenylalkyl, phenyl, substituted phenyl, $C_3$ to $C_7$ cycloalkyl, and $C_3$ to $C_7$ substituted cycloalkyl;

$R^4$ is selected from the group consisting of a hydrogen atom, $C_1$ to $C_{10}$ alkyl, $C_2$ to $C_{10}$ alkenyl, benzyl, substituted benzyl, naphthylmethyl, and substituted naphthylmethyl;

$R^5$ is selected from the group consisting of a hydrogen atom, $C_1$ to $C_{10}$ alkyl, $C_2$ to $C_{10}$ alkenyl, benzyl, substituted benzyl, naphthylmethyl, and substituted naphthylmethyl;

X is a sulfur atom(S);

Y is selected from the group consisting of a nitrogen atom (N) and an oxygen atom (O);

Z is a hydrogen atom;

m is zero to five;

n is zero to four; and p is zero or one, provided that when Y is nitrogen, p is one and further provided that when Y is oxygen p is zero and Z is hydrogen, or a pharmaceutically-acceptable salt thereof.

19. A method for the preparation of the composition of claim 1, comprising the following steps:

(a) coupling a first amino acid with a protected ∝-amino group and having side chain $R^1$ to a functionalized resin to obtain a resin-bound amino acid;

(b) deprotecting the amino-terminus of said resin-bound amino acid;

(c) coupling a second amino acid with a protected ∝-amino group and having side chain $R^3$ to said resin-bound amino acid to obtain a resin-bound dipeptide;

(d) deprotecting the amino-terminus of said resin-bound dipeptide; and (e) cyclizing the resin-bound dipeptide to form a hydantoin, wherein steps (a) through (e) are performed on at least one mixture of two or more of the first or the second said amino acids to obtain a library of two or more hydantoin compounds.

20. The method of claim 19, wherein the cyclization step is performed using triphosgene.

21. The method of claim 19, wherein the cyclization step is performed using thiocarbonydiimidazole to obtain library of thiohydantoin compounds.

22. The method of any one of claims 19, 19, or 20, further comprising alkylating the amine component of the functionalized amine resin after step (a) and prior to step (b).

23. The method of any one of claims 19, 19, or 20, further comprising alkylating the active nitrogen in the hydantoin ring after step (e).

24. The method of any one of claims 19, 19, or 20, further comprising alkylating at the carbon atom having side chain $R^3$.

25. The method of claim 19, further comprising cleaving the hydantoin library from the resin.

* * * * *